(12) United States Patent
Chunchanakatte Melukote et al.

(10) Patent No.: US 12,115,094 B1
(45) Date of Patent: Oct. 15, 2024

(54) WEARABLE ARMREST APPARATUSES

(71) Applicant: Wishnew LLC, Skillman, NJ (US)

(72) Inventors: Akhil Krishna Chunchanakatte Melukote, Skillman, NJ (US); Sonika Pulluru, Hyderabad (IN); Lingala Mani Teja, Pradesh (IN); Polisetti Lakshmi Manikanta, Palakol (IN)

(73) Assignee: WISHNEW LLC, Skillman, NJ (US)

( * ) Notice: Subject to any disclaimer, the term of this patent is extended or adjusted under 35 U.S.C. 154(b) by 0 days.

(21) Appl. No.: 18/628,754

(22) Filed: Apr. 7, 2024

(51) Int. Cl.
*A61F 5/01* (2006.01)
*A61F 5/37* (2006.01)
*A45F 3/00* (2006.01)

(52) U.S. Cl.
CPC .......... *A61F 5/0118* (2013.01); *A61F 5/3723* (2013.01); *A45F 3/005* (2013.01)

(58) Field of Classification Search
CPC ... A61G 7/075; A61G 13/1235; A61F 5/3715; A61F 5/3723; A61F 5/0118; A61F 5/05858; A61F 5/37; A61F 5/373; A61F 5/3738; A61F 5/3753; A47D 13/029; A45F 3/005; A45F 2003/144; A41D 2400/482
See application file for complete search history.

(56) References Cited

U.S. PATENT DOCUMENTS

| | | | |
|---|---|---|---|
| 1,267,142 A | 5/1918 | Stowers et al. | |
| 2,358,551 A | 9/1944 | Beaton | |
| 2,560,243 A | 7/1951 | Peterson | |
| 3,338,236 A | 8/1976 | McLeod, Jr. | |
| 4,751,923 A | 8/1988 | Marino | |
| 5,086,762 A | 2/1992 | Chee | |
| 5,385,322 A | 1/1995 | Kim et al. | |
| 5,395,306 A | 3/1995 | Bauerfeind et al. | |
| 6,190,340 B1 | 2/2001 | Borell et al. | |
| 6,315,747 B1 | 11/2001 | Toole | |
| 6,755,799 B2 | 6/2004 | Toda | |
| 7,871,388 B2 | 1/2011 | Brown | |
| 9,044,324 B2 | 6/2015 | Krenzel | |
| 9,226,845 B2 | 1/2016 | Troncoso | |
| D755,981 S | 5/2016 | Shamaiengar | |

(Continued)

OTHER PUBLICATIONS

Sittingbridge. "napwrap™ Your personal armrest." Kickstarter. https://www.kickstart er.com/projects/1997355283/napwraptm-your-personal-armrest. Accessed on Dec. 28, 2023.

(Continued)

*Primary Examiner* — Keri J Nelson

(57) ABSTRACT

This disclosure relates to wearable armrest apparatuses and methods of using the same. The wearable armrest apparatuses are adapted to be worn around individuals' waists or torsos, and they include armrest structures that can support the individuals' elbows and/or forearms. The wearable armrest apparatuses are able to support the individuals' elbows and/or forearms when performing various types of tasks, including tasks that are performed in standing positions or which require mobility. The wearable armrest apparatuses can be arranged in an ergonomic design that reduces strain on shoulder, neck, and back regions in a more effective manner compared to traditional armrests that are incorporated into seating assemblies. Other embodiments are disclosed herein as well.

20 Claims, 15 Drawing Sheets

(56) References Cited

U.S. PATENT DOCUMENTS

| | | | |
|---|---|---|---|
| 9,700,152 B2* | 7/2017 | Telford | A47D 13/025 |
| 9,827,133 B1 | 11/2017 | Krenzel | |
| 10,406,014 B2 | 9/2019 | Collier et al. | |
| 10,610,400 B1 | 4/2020 | Krenzel | |
| 11,045,342 B2 | 6/2021 | Doyle | |
| 2005/0273026 A1* | 12/2005 | Howard | A61F 5/3753 |
| | | | 602/20 |
| 2016/0022468 A1* | 1/2016 | Lo | A61F 5/05858 |
| | | | 602/20 |
| 2016/0113406 A1 | 4/2016 | Shamaiengar | |
| 2017/0056232 A1 | 3/2017 | Yeung | |

OTHER PUBLICATIONS

Skelex B.V. "Skelex 360-XFR." https://skelex.com/skelex-360-xfr/. Accessed on Feb. 20, 2024.

Tynor. "Tynor Elbow Support." Amazon. https://www.amazon.com/TYNOR-Tynor-Elbow-Support/dp/B017KOAG6A. Accessed on Feb. 20, 2024.

Tynor. "Tynor ROM Elbow Brace." NavaFresh. https://navafresh.com/products/tynor-rom-elbow-brace-black-left-universal-size-1-unit?gad_source=1&gclid=CjwKCAiAlcyuBhBnEiwAOGZ2S2FkKOLSh4vzlAhxtOwluFC76GshmxuoebvUuCWI6twUVf8dONnurBoC4y0QAvD_BwE. Accessed on Feb. 20, 2024.

Herowear LLC. "Apex Exosuit." Core77 Design Awards 2021. https://designawards.core77.com/Commercial-Equipment/104566/Apex-Exosuit. Accessed on Feb. 20, 2024.

Kakum. "Kakum: Adjustable wrist rest for mouse users." Indiegogo. https://www.indiegogo.com/projects/kakum-adjustable-wrist-rest-for-mouse-users#/. Accessed on Feb. 20, 2024.

Sara Hendren. "jennifer crupi's 'unguarded gestures'". Abler. http://abler.siteleaf.net/jennifer-crupis-unguarded-gestures/. Accessed on Feb. 20, 2024.

* cited by examiner

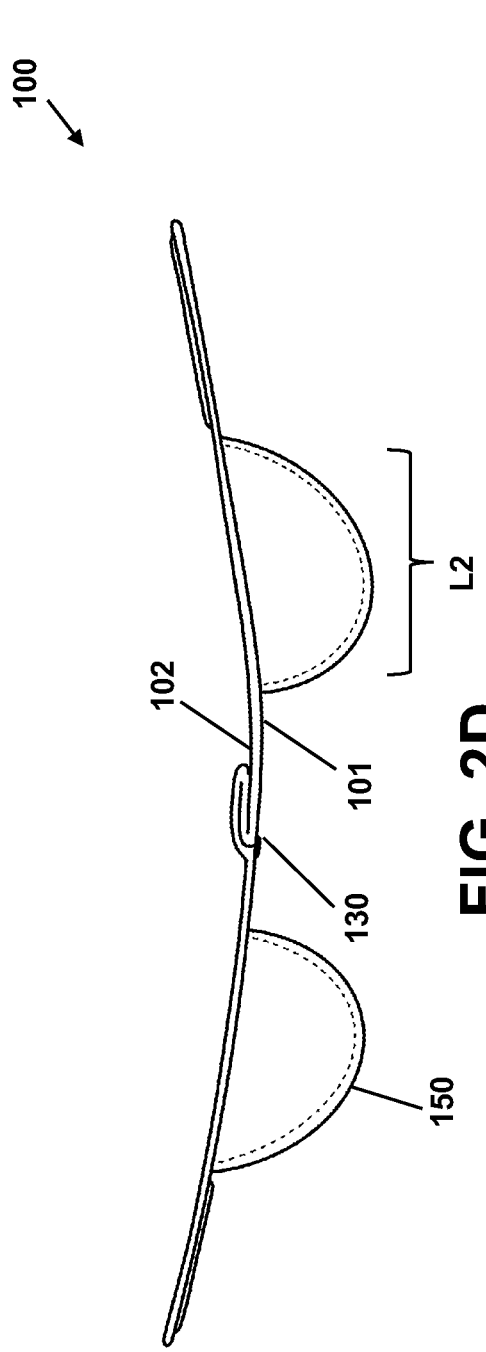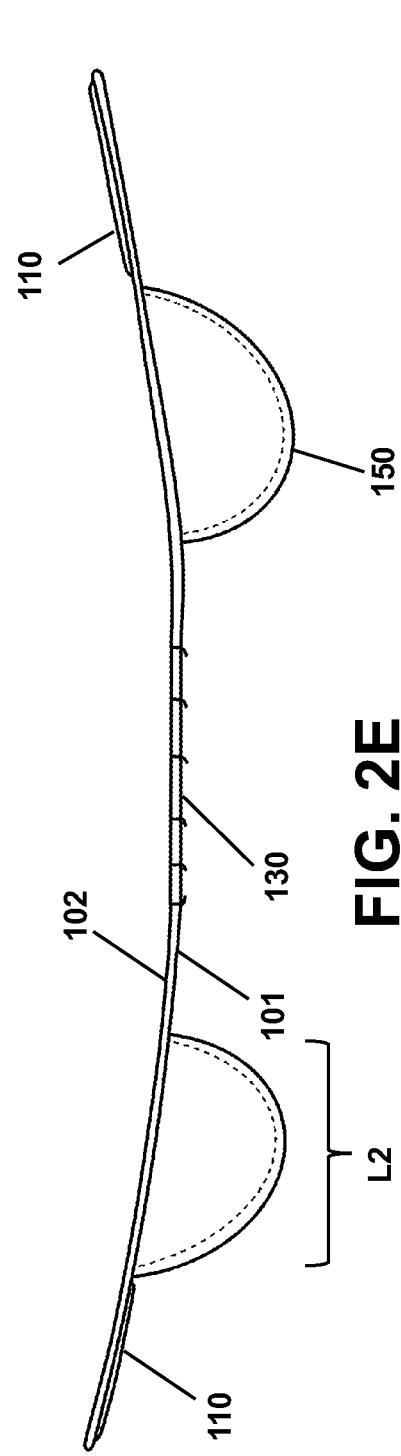

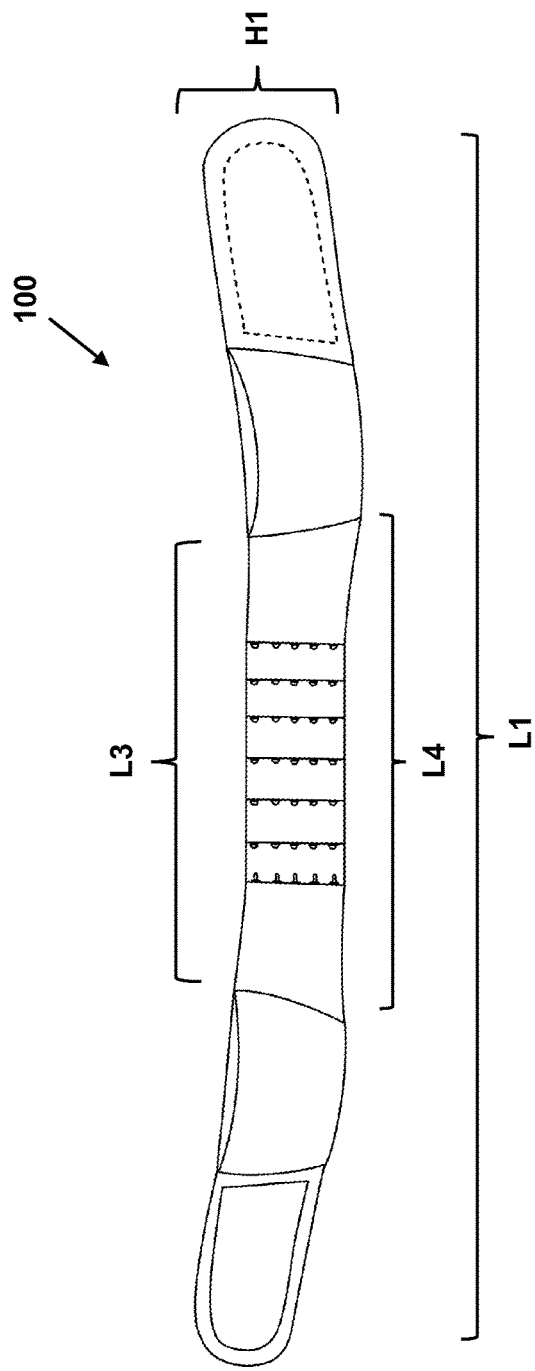
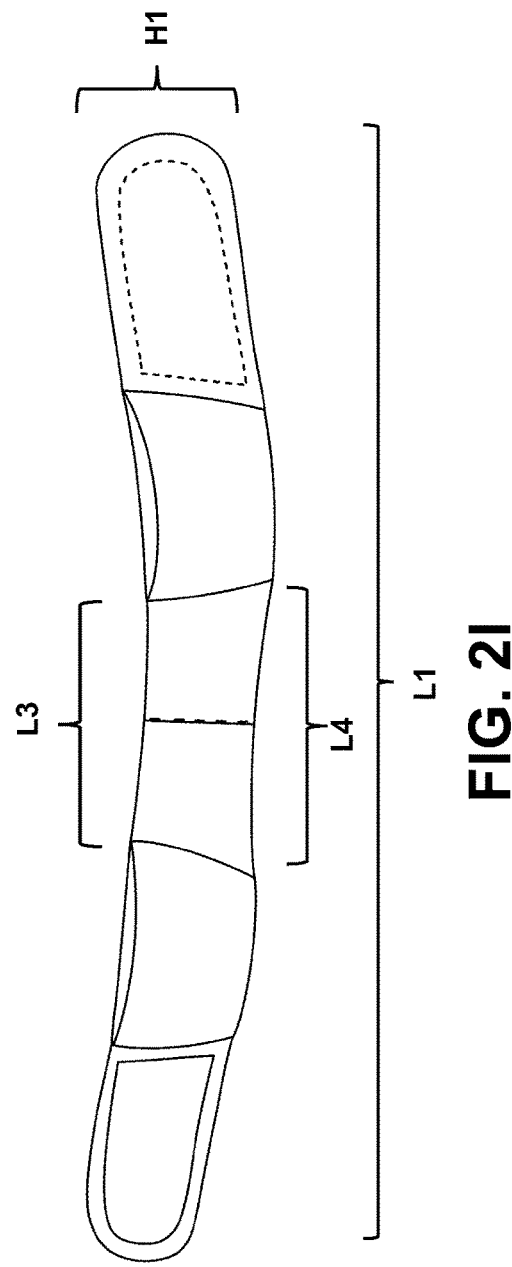
FIG. 2H
FIG. 2I

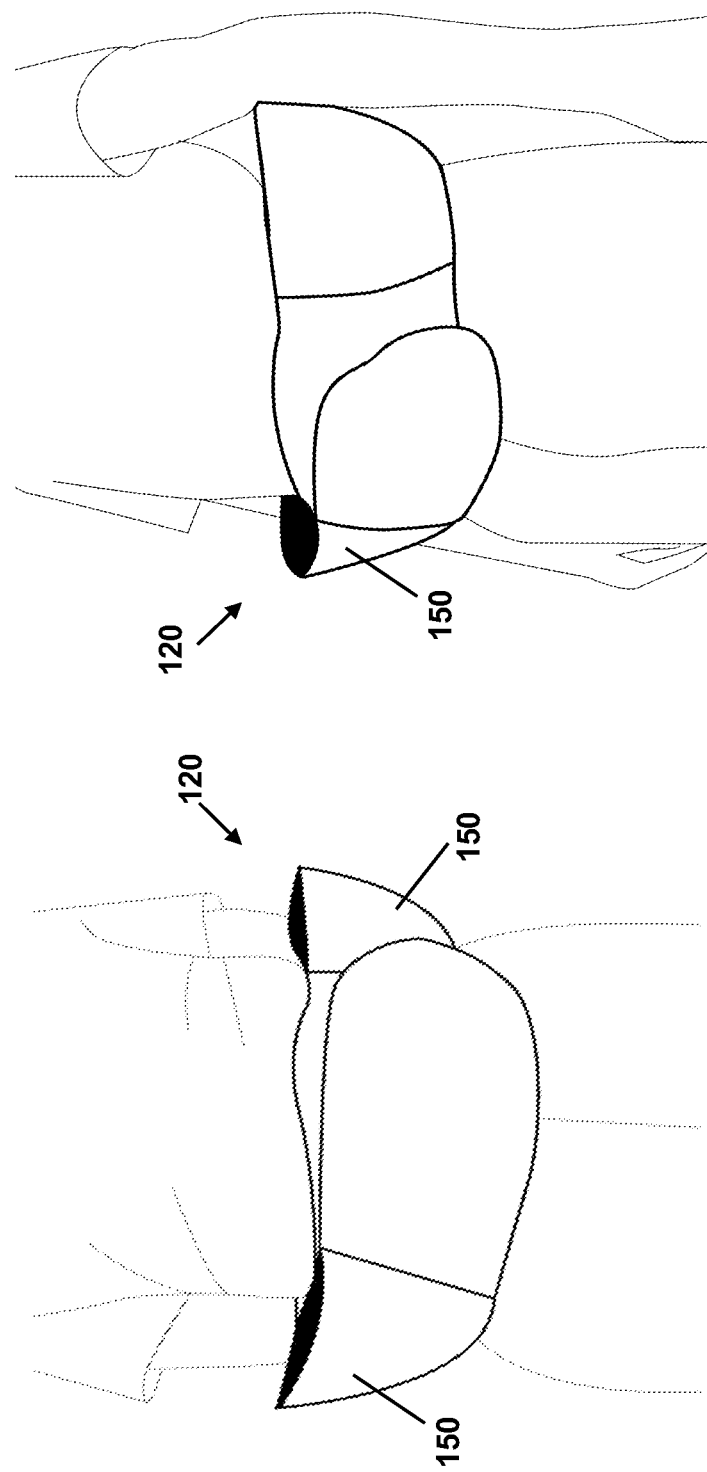

WEARABLE ARMREST APPARATUSES

TECHNICAL FIELD

This disclosure is related to wearable armrest apparatuses and related methods. In certain embodiments, the wearable armrest apparatuses can provide support for an individual's elbows and/or forearms while performing various activities. Additionally, an ergonomic design of the wearable armrest apparatuses enables the wearable armrest apparatuses to be worn comfortably on or around an individual's waist or torso region.

BACKGROUND

Traditionally, armrests are integrated into chairs, recliners, couches, sofas, or similar types of external seating structures, and an individual is typically required to be seated in those structures to utilize the armrests. Because these traditional armrests are integrated into external or stationary objects, an individual is unable to utilize the armrest structures when performing activities in a standing position or performing activities that are mobile in nature. For example, traditional armrests cannot be utilized in scenarios where an individual is performing work at a standing desk station (e.g., a desk designed to be used by a person standing upright), which typically requires the individual's arms to be extended forward for lengthy time periods without any support. Likewise, traditional armrests cannot be utilized in scenarios where individuals are engaging in activities of a mobile nature, such as preparing food, cutting vegetables, fishing, etc. In these and other scenarios, the individual's arms can be unsupported for extended periods of time.

Additionally, the designs of traditional armrests are plagued with certain ergonomic deficiencies. Utilizing traditional armrest structures integrated into seating structures and/or other external objects typically requires some displacement of an individual's elbow in an upward or sidewards direction. For example, utilizing armrests integrated into a desk chair, or similar type of seating apparatus, typically requires an individual to displace his or her elbows outward to engage the armrests. This displacement of the arms can cause strain on the individual's shoulder joint and/or corresponding musculoskeletal system in the shoulder region.

Accordingly, there is a need for improved armrest solutions that overcome some or all of the shortcomings mentioned above.

BRIEF DESCRIPTION OF DRAWINGS

To facilitate further description of the embodiments, the following drawings are provided, in which like references are intended to refer to like or corresponding parts, and in which:

FIG. 2D is another top view of the wearable armrest apparatus illustrated in FIG. 2A with the size-adjustment feature arranged in a retracted or engaged configuration in accordance with certain embodiments;

FIG. 2E is another top view of the wearable armrest apparatus illustrated in FIG. 2A with the size-adjustment feature arranged in an extended or disengaged configuration in accordance with certain embodiments;

FIG. 2H is another front view of the wearable armrest apparatus illustrated in FIG. 1A in accordance with certain embodiments;

FIG. 2I is another front view of the wearable armrest apparatus illustrated in FIG. 1A in accordance with certain embodiments;

FIG. 3C illustrates a wearable armrest apparatus being worn by an individual with the individual's arms in a rearward position in accordance with certain embodiments;

FIG. 3D illustrates a wearable armrest apparatus being worn by an individual with the individual's arms in a side or hanging position in accordance with certain embodiments;

Figure 1A:
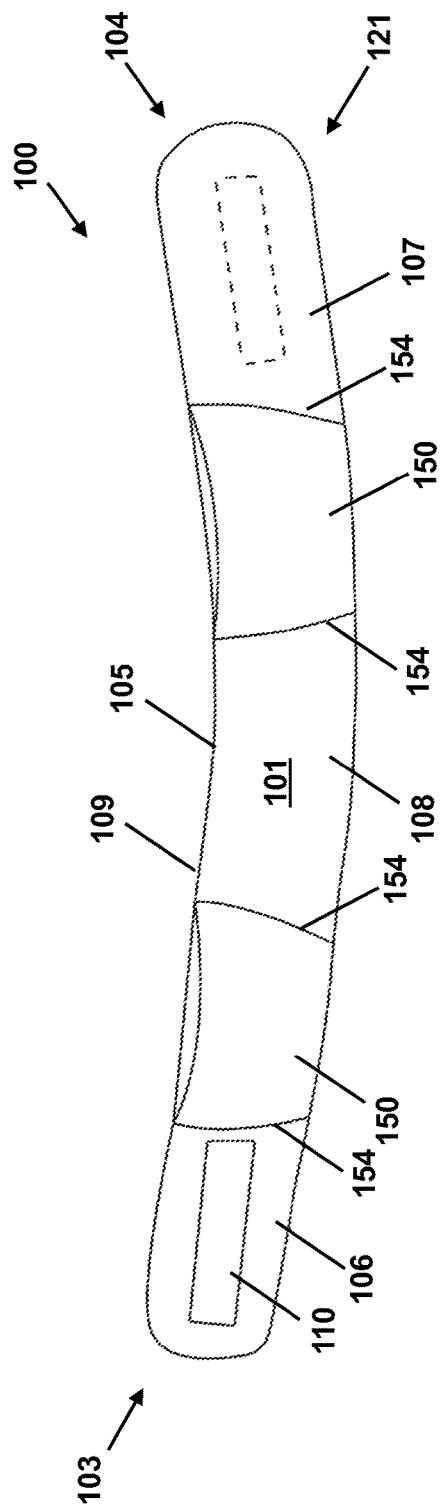
FIG. 1A is a front view of a wearable armrest apparatus arranged in a disassembled configuration in accordance with certain embodiments.
Figure 1B:
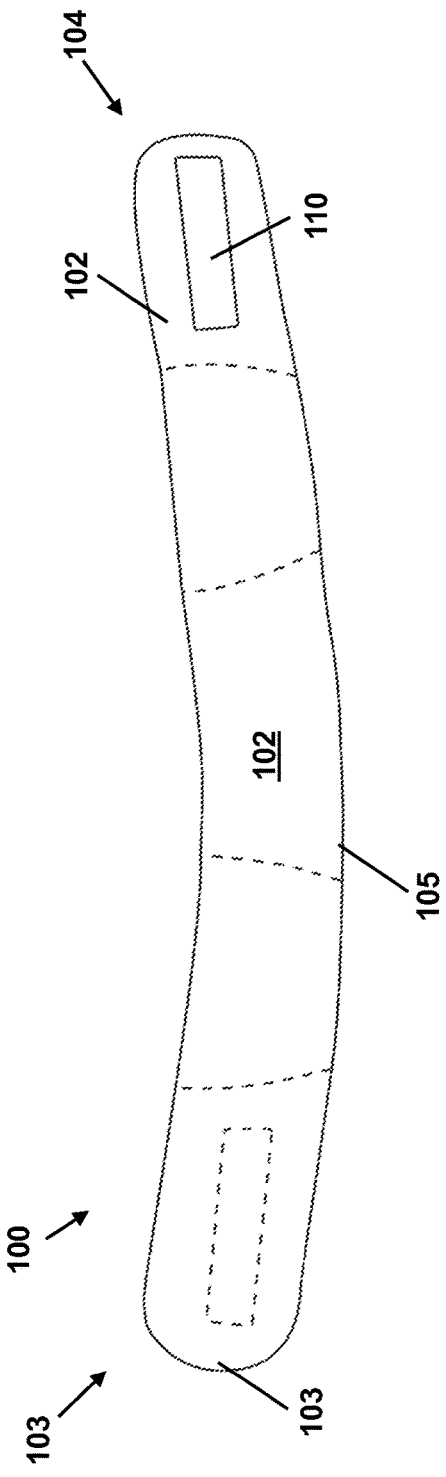
FIG. 1B is a rear view of the wearable armrest apparatus illustrated in FIG. 1A in accordance with certain embodiments.
Figure 1C:
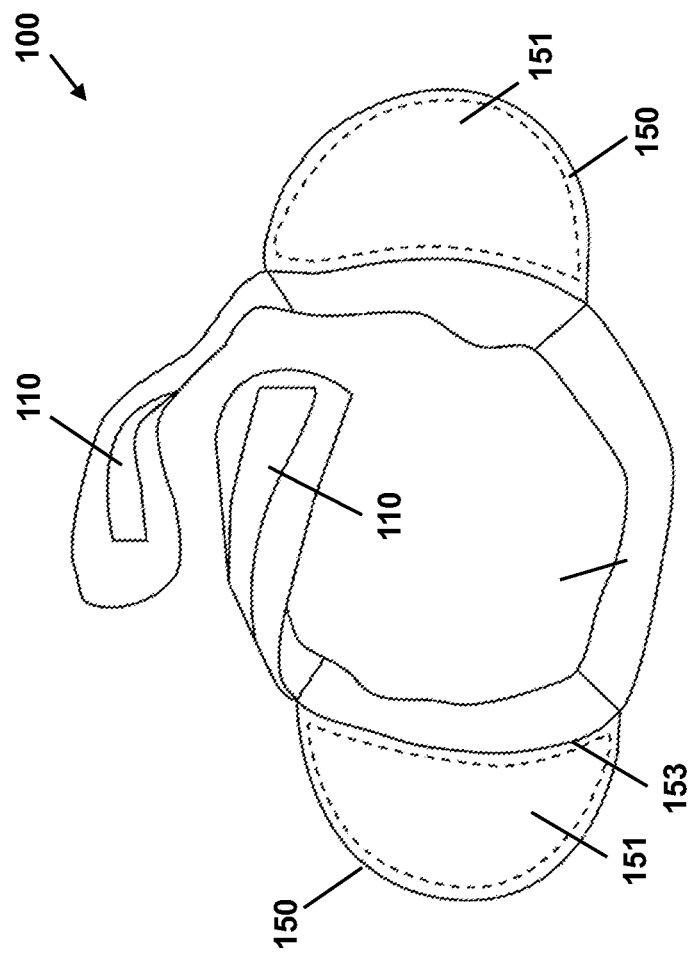
FIG. 1C is a top view of the wearable armrest apparatus illustrated in FIG. 1A in accordance with certain embodiments.
Figure 1D:
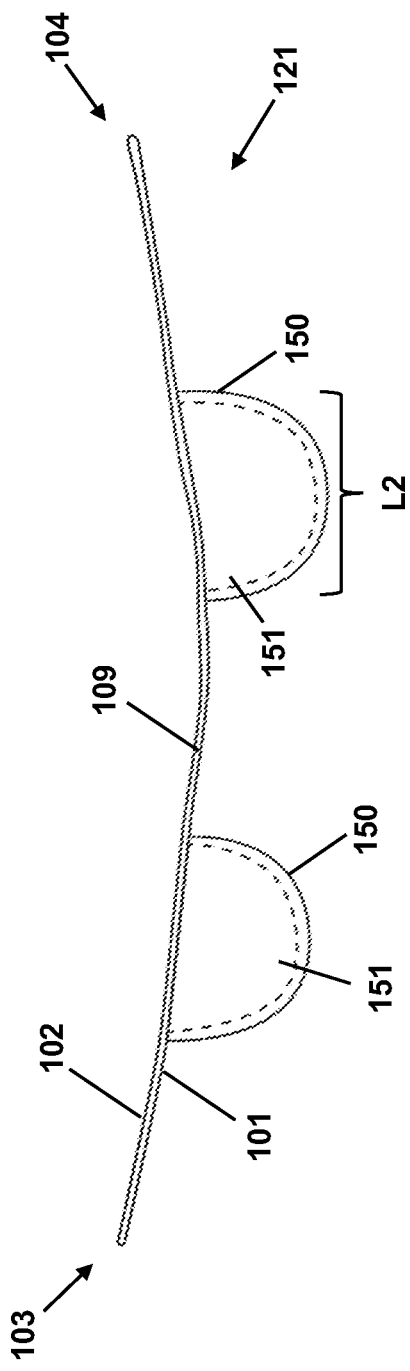
FIG. 1D is another top view of the wearable armrest apparatus illustrated in FIG. 1A in accordance with certain embodiments.
Figure 1E:
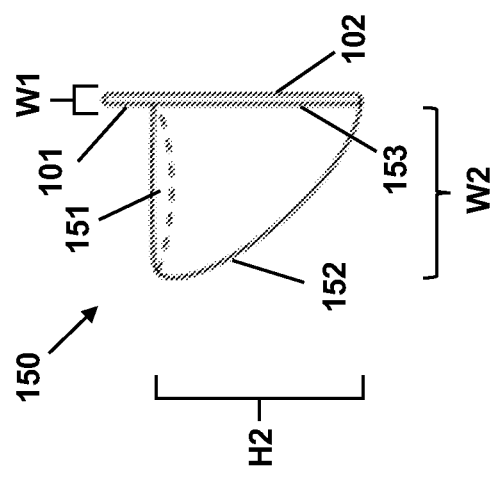
FIG. 1E is side view of the wearable armrest apparatus illustrated in FIG. 1A in accordance with certain embodiments.
Figure 1F:
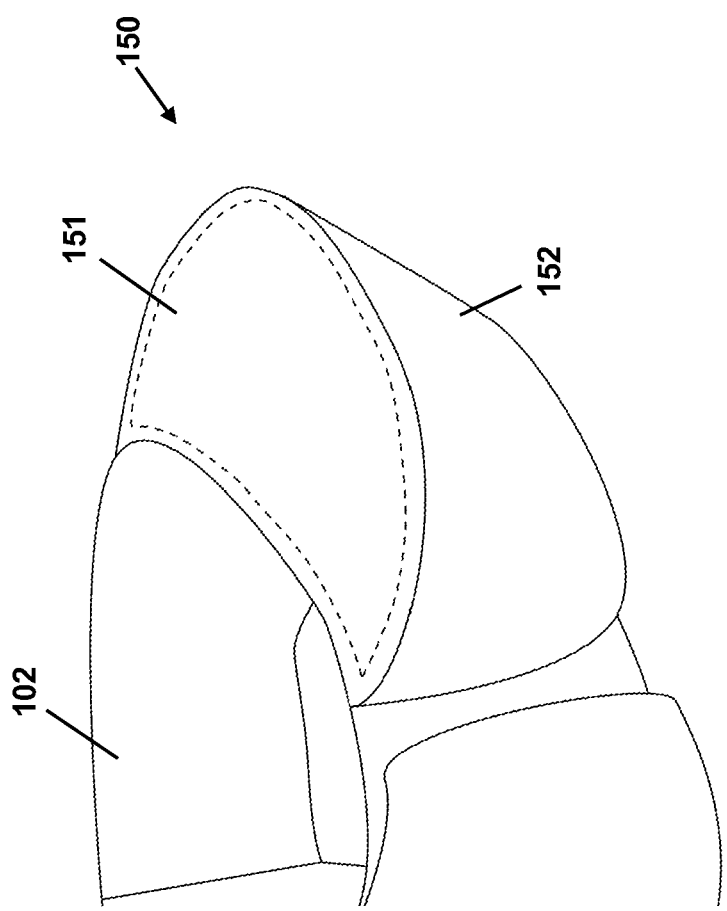
FIG. 1F is perspective view illustrating details of an exemplary armrest structure of the wearable armrest apparatus illustrated in FIG. 1A in accordance with certain embodiments.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein.

The terms "left," "right," "front," "rear," "back," "top," "bottom," "over," "under," "proximal," "distal," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

As used herein, the terms "approximately" or "substantially" can, in some embodiments, mean within plus or minus ten percent of the stated value. In other embodiments, "approximately" or "substantially" can mean within plus or minus five percent of the stated value. In further embodiments, "approximately" or "substantially" can mean within plus or minus three percent of the stated value. In yet other embodiments, "approximately" or "substantially" can mean within plus or minus one percent of the stated value.

DETAILED DESCRIPTION OF EXEMPLARY EMBODIMENTS

The present disclosure relates to apparatuses, assemblies, devices, systems, and methods for wearable armrest solutions. In certain embodiments, a wearable armrest apparatus comprises at least one armrest structure (and, in many cases, a pair of armrest structures) coupled to a strap portion that is adapted to be worn around an individual's waist or abdominal region. In an operational or assembled configuration, the wearable armrest apparatus can be equipped to an individual's body and the armrest structures attached to the strap portion can be situated directly beneath the individual's elbows (and/or portions of the individual's forearms) and directly adjacent to the individual's body. In this configuration, a distal end and proximal end of the strap portion can include connectors that can be coupled together to secure the wearable armrest apparatus to the individual's body. The connectors located on the distal and proximal ends of the strap portion can be disengaged or decoupled from each other to facilitate removal of the wearable armrest apparatus from the individual's body.

The wearable armrest apparatus provides a variety of advantages. Amongst other things, the ergonomic design of the wearable armrest apparatus permits an individual to comfortably rest and support their elbows and/or arms while performing various activities, such as activities that may require or involve the individual to extend their arms in a forward position (e.g., activities such as operating computing devices, preparing food, eating, reading documents or books, holding a fishing rod, etc.). In some embodiments, the solutions described herein essentially decouple armrest structures from external objects (e.g., such as seating structures) and integrate those armrest structures into wearable or mobile apparatuses to provide an individual with arm support in standing positions and/or in performing tasks that require mobility.

Additional benefits can be attributed to the body-molding or body-hugging design of the wearable arm apparatuses. For example, in some embodiments, the armrest structures coupled to the strap portion of a wearable armrest apparatus can include concave inner surfaces adapted to engage and accommodate the side regions of individual's having differing body types and dimensions. Additionally, in some embodiments, the strap portion can include a size-adjustment feature that enables the size of the strap portion to be adjusted to accommodate individuals having different waist or torso sizes. Moreover, the size-adjustment feature enables the armrest structures included on the strap portion to be precisely positioned in optimal locations directly beneath an individual's elbows or forearms, which provides a distinct ergonomic advantage compared to existing armrests that typically require displacement of an individual's arms in various directions to rest his or her elbows on the armrests.

The apparatuses described herein effectively decouple armrest structures from the external objects (such as seating assemblies, desks, etc.) and directly couple the armrest structures to a user's body. In this manner, the apparatuses operate as mobile armrests that move with individuals as they are performing tasks that cannot be performed in seated positions. Additionally, the adjustability of the apparatuses enables elbow and arm support structures to be situated in ideal positions, regardless of the users' body type or dimensions.

The wearable armrest apparatuses can reduce strain on an individual's shoulder joints, neck, upper back, and/or the musculoskeletal system in these bodily regions. Additionally, the wearable armrest apparatuses can reduce strain on these bodily regions in a more effective manner compared to traditional armrests that are incorporated into external objects, such as seating assemblies. As mentioned above, utilizing the traditional armrest structures incorporated into these external objects requires some displacement of an individual's elbow or forearm (e.g., in an upward or sidewards direction) away from a neutral position abutting the individual's body. In contrast, the armrest support structure of the wearable armrest apparatuses can be situated directly adjacent to the individual's waist or abdominal region and, therefore, permit the individual's elbows and forearms to be supported directly adjacent to the individual's body beneath the elbow or forearm region (without any lateral or vertical displacement of the individual's arms). This improved arrangement provides a more ergonomic and comfortable solution for supporting an individual's arms and is more effective in reducing the strain imposed on the individuals' shoulder, neck and upper back regions.

The wearable armrest apparatuses discussed herein can be used in a variety of different contexts and environments. In one exemplary scenario, the wearable armrest apparatus can provide arm support when an individual's arms are extended to operate a computing device, review documents, or perform other activities in a standing position (e.g., such as where the computing device or documents are rested on a surface of a standing or adjustable-height desk that raises the computing device in an elevated position). In another exemplary scenario, the wearable armrest apparatus can provide arm support when an individual is sitting in a seating assembly that does not have armrest structures. In another exemplary scenario, the wearable armrest apparatus can provide arm support when an individual is preparing food or cutting vegetables. In another exemplary scenario, the wearable armrest apparatus can provide arm support when an individual's arms are extended to hold or operate a fishing rod. The wearable armrest apparatus can provide arm support in many other scenarios as well.

The embodiments described in this disclosure can be combined in various ways. Any aspect or feature that is described for one embodiment can be incorporated to any other embodiment mentioned in this disclosure.

FIGS. 1A-1G illustrate an exemplary wearable armrest apparatus 100 according to certain embodiments. FIGS. 2A-2I illustrate another exemplary wearable armrest apparatus 100 that includes a size-adjustment assembly 130 according to certain embodiments. The features of the wearable armrest apparatuses 100 illustrated in FIGS. 1A-1G and 2A-2I are jointly discussed below.

The wearable armrest apparatus 100 comprises, inter alia, a strap portion 105 and a pair of armrest structures 150 connected or attached to an exterior surface 101 of the strap portion 105. As explained throughout this disclosure, the strap portion 105 of the wearable armrest apparatus 100 can be worn around an individual's waist or torso region, and the armrest structures 150 can be situated beneath the individual's elbow or forearms to provide support the individual's elbow and/or forearms while performing various activities (e.g., operating a desktop or laptop computing device, operating a mobile device, preparing food, holding a fishing pole, etc.). As explained below, the wearable armrest apparatus 100 can be outfitted with several form-fitting features that enable the wearable armrest apparatus 100 to be adjusted and comfortably worn by individuals of different body types and sizes.

Figure 3A:
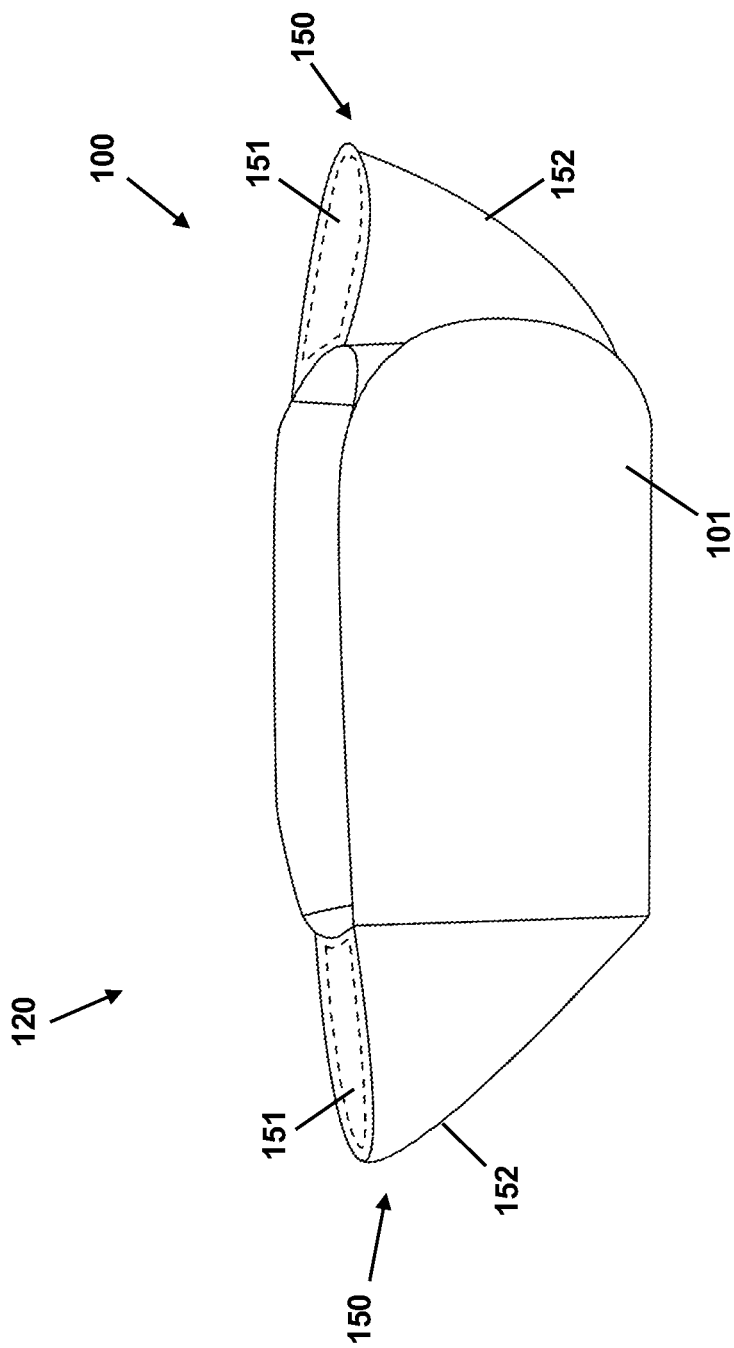
FIG. 3A is a front view of a wearable armrest apparatus arranged in an assembled configuration in accordance with certain embodiments.
Figure 3B:
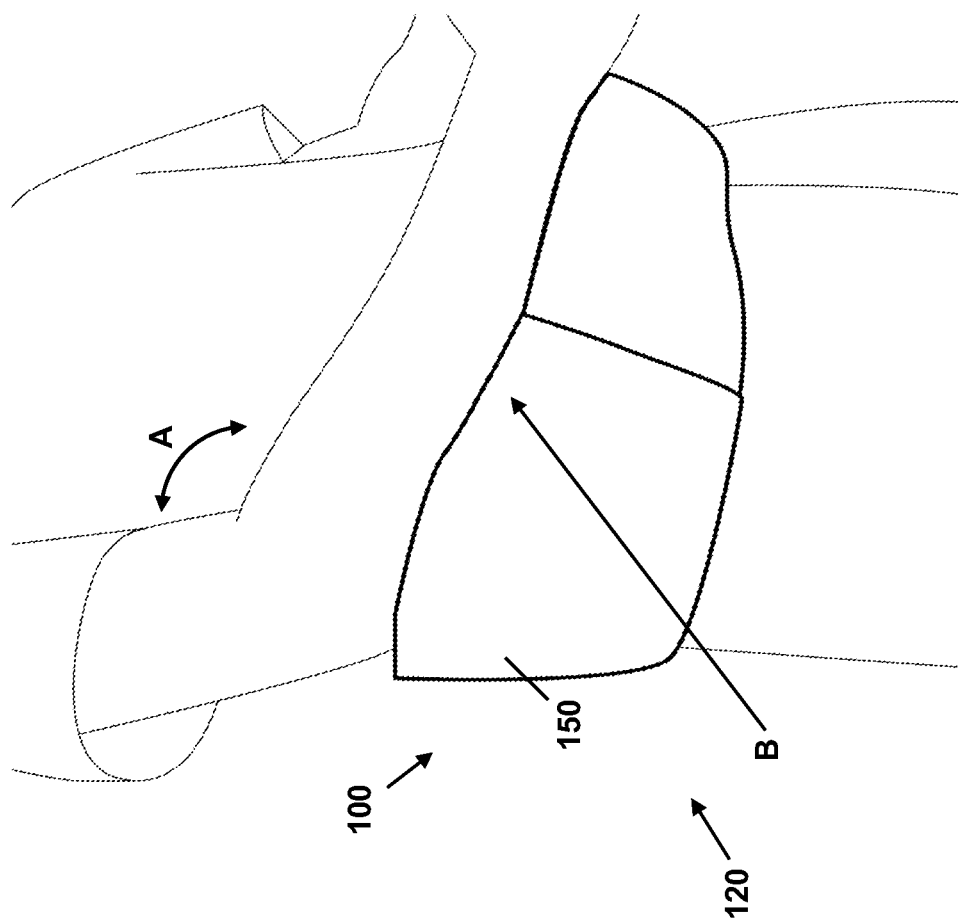
FIG. 3B illustrates a wearable armrest apparatus being worn by an individual with the individual's arms in an extended position in accordance with certain embodiments.
Figure 3E:
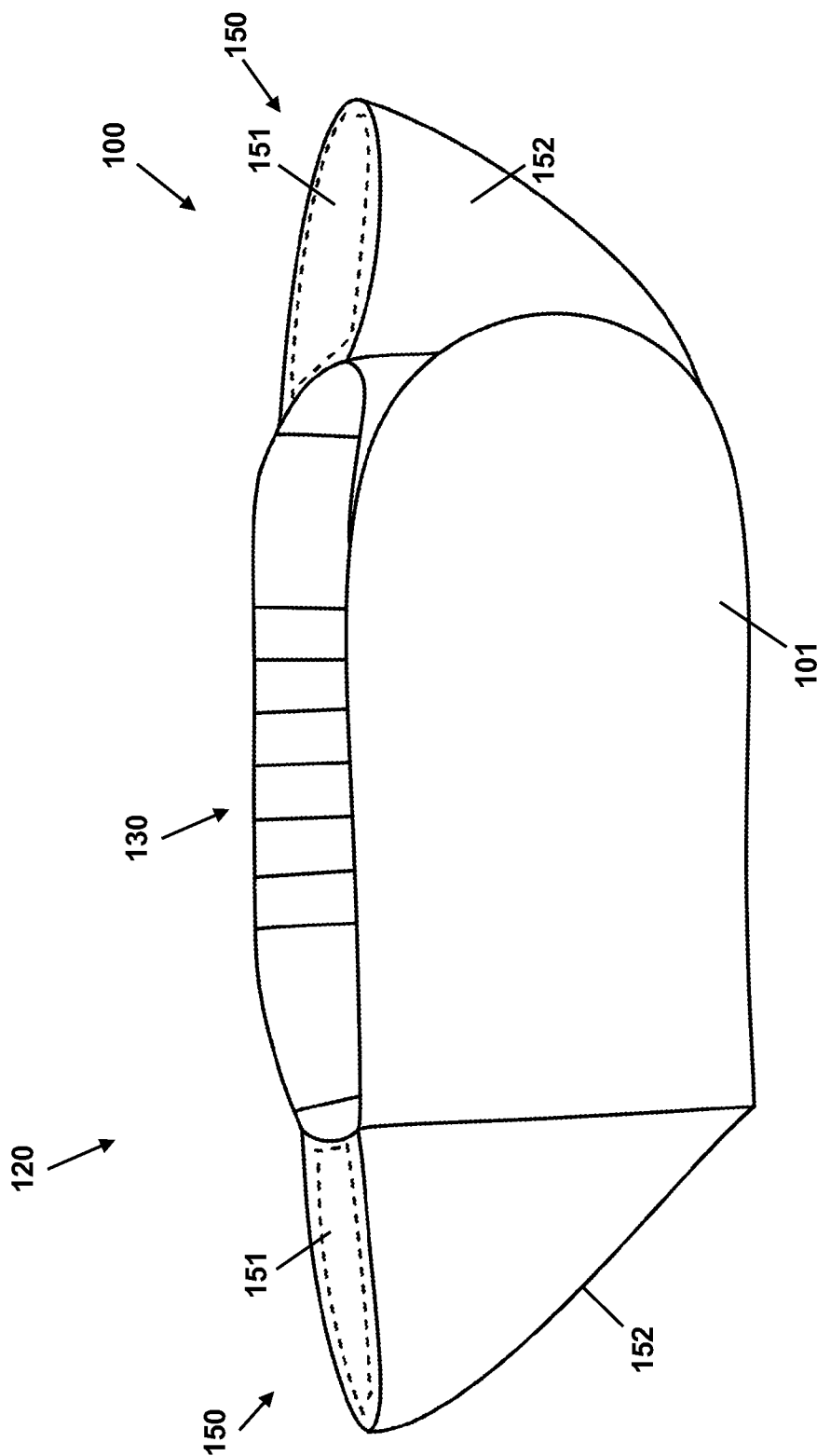
FIG. 3E is a front view of another wearable armrest apparatus arranged in an assembled configuration in accordance with certain embodiments.

The strap portion 105 of the wearable armrest apparatus 100 includes an exterior surface 101 and interior surface 102. When the wearable armrest apparatus 100 is equipped to an individual in an assembled configuration (e.g., as shown in FIGS. 3B-3D), the exterior surface 101 faces outwardly with respect to the individual and the interior surface 102 faces inwardly toward the individual. In some embodiments, the exterior surface 101 and the interior surface 102 are opposites sides of the same piece of fabric or material. In other embodiments, the exterior surface 101 and the interior surface 102 may be included on separate pieces of fabric or materials that are situated adjacent and parallel to each other.

An edge 109 is formed around the perimeter of the strap portion 105 and defines the boundaries of the strap portion 105. The edge 109 can include a small surface that corresponds to the outer periphery of the exterior surface 101 and/or interior surface 102, or the location where the exterior or interior surfaces terminate. In certain embodiments, the edge 109 can surround the entire circumference of the strap portion 105. In other embodiments, the edge 109 may include gaps in areas where the armrest structures 150 are located.

The dimensions of the strap portion 105 can vary. In some embodiments, the strap portion 105 (and exterior surface 101 and interior surface 102) has a length L1 (see FIGS. 1G and 2H-2I) extending from a proximal end 103 to a distal end 104, a height H1 (see FIGS. 1G and 2H-2I) extending from a lower portion of the edge 109 to an upper portion of the edge 109 (e.g., from a lower edge 109 to an upper edge 109), and a width W1 (see FIGS. 1E and 2F) that corresponds to the surface size of the edge 109 and/or which corresponds to the thickness or distance between the exterior surface 101 and the interior surface 102.

The length L1, height H1, and width W1 of the strap portion 105 can vary. In some examples, the length L1 can be approximately 48 inches and/or within a range of 36-60 inches. Moreover, as explained below, a size-adjustment feature 130 can be configured to adjust the length L1 of the strap portion 105 to fit an individual's waist or torso. In some examples, the height H1 of the strap portion 105 can be approximately 5.5 inches, 6 inches and/or within a range of 3-12 inches, and the width W1 can be in a range from 0.001 inches to 0.5 inches depending on the materials used to construct the strap portion 105 (and/or the materials used to construct the exterior surface 101 and interior surface 102). The strap portion 105 can be adapted to have other dimensions as well.

The strap portion 105, including the exterior surface 101 and/or interior surface 102, can be constructed of various materials. In some embodiments, the strap portion 105 can be constructed of one or more of the following materials: cotton fibers, synthetic fibers (e.g., nylons, polyesters, spandex, polyurethanes, etc.), wool fibers, linen fibers, microfibers, rayon, denim, leather, and/or fleece. In some embodiments, the strap portion 105 (or certain segments of the strap portion 105) can be constructed of a flexible or stretchable materials, such as spandex, lycra, elastane, modal, tencel, merino wools, stretchable cottons, etc., to aid the wearable armrest apparatus 100 in accommodating individual's having different body types, shapes, and sizes. In some embodiments, the strap portion 105 (or certain segments of the strap portion 105) can be constructed of breathable materials, such as cotton and/or linen, that promote ventilation, permit air and/or moisture to pass through the strap portion 105, and prevent overheating or moisture buildup.

The exterior surface 101 of the strap portion can include a proximal exterior segment 106, a distal exterior segment 107, and a middle exterior segment 108 that are separated by the armrest structures 150. In particular, the proximal exterior segment 106 can include a portion of the exterior surface 101 that extends between the proximal end 103 and a first armrest structure 150 (or a connecting edge 154 of the first armrest structure 150 located nearest to the proximal end 103). The distal exterior segment 107 can include a portion of the exterior surface 101 that extends between the distal end 104 and a second armrest structure 150 (or a connecting edge 154 of the second armrest structure 150 located nearest to the distal end 104). The middle exterior segment 108 can include a portion of the exterior surface 101 located between the armrest structures 150 (or located between inner connecting edges 154 of two armrest structures 150).

In some embodiments, the interior surface 102 can include corresponding segments (e.g., a proximal interior segment, a distal interior segment, and a middle interior segment) directly opposite the proximal exterior segment 106, distal exterior segment 107, and middle exterior segment 108 on the exterior surface 102. In other embodiments, the interior surface 102 can include a single, contiguous surface that extends from the proximal end 103 to the distal end 104.

In some embodiments, the strap portion 105 and/or exterior surface 101 can include a single contiguous surface or piece of material, and the armrest structures 150 can be attached to the exterior surface 101. In other embodiments, the exterior surface 101 can include a plurality of segments that are joined or connected together to form the exterior surface 101. For example, in some cases, the proximal exterior segment 106, distal exterior segment 107, and middle exterior segment 108 can be separate pieces of material that are connected to side edges of the armrest structures (e.g., at or near connecting edges 154) to form the exterior surface 101.

The strap portion 105 can include one or more connectors 110 that enable the proximal end 103 of the strap portion 105 to be connected or coupled to the distal end 104 of the strap portion 105 in a loop configuration, which can be worn around an individual's waist or torso region (see e.g., FIGS. 3A-3E). The strap portion 105 can be outfitted with any appropriate connector(s) 110 to facilitate a connection of the proximal end 103 to the distal end 104.

The exemplary wearable armrest apparatuses 100 shown in FIGS. 1A-1G and 2A-2I include two connectors that are configured to engage each other to form a releasable or detachable connection. More specifically, a first connector 110 is located on the exterior surface 101 on or near a proximal end 103 (e.g., on the proximal exterior segment 106) of the strap portion 105, and the second connector 110 is located on the interior surface 102 on or near the distal end 103 of strap portion 105. In this example, the wearable armrest apparatus 100 can be arranged in an assembled configuration 120 (see, e.g., FIGS. 3A-3E) and worn around an individual's waist or torso region by situating or placing the proximal end 103 near the front of the individual's body (such that the first connector 110 is facing outwardly from the individual) and then subsequently folding or placing distal end 103 of the strap portion 105 on top of the proximal end (such that the second connector 110 faces inwardly toward the individual and such that the second connector 110 is aligned with the first connector 110 to facilitate a connection between the two connectors).

Various types of connectors 110 and connection schemes can be utilized to arrange the wearable armrest apparatus 100 in an assembled configuration 120. In some preferred embodiments, the connectors 110 included on the wearable armrest apparatus 100 can include a corresponding pair of hook-and-loop connectors (e.g., Velcro® connectors) to couple the proximal end 103 to the distal end 104. Additionally or alternatively, the connectors 110 can include one or more of the following: one or more button connectors (e.g., such that one end of the strap portion includes one or multiple buttons and a second end of the strap portion includes one or more openings or holes for receiving the buttons); one or more zipper connectors (e.g., such that one end of the strap portion includes a first portion of a zipper connector and an opposite end of the strap portion includes a second portion of the zipper connector); one or more snap connectors (e.g., such that one end of the strap portion includes one or multiple male snap connectors and a second end of the strap portion includes one or more female snap connectors); one or more tie connectors (e.g., such that each end of the strap portion includes one or more strings or extensions that can be knotted or tied together); one or more magnetic connectors (e.g., such that one end of the strap portion 105 includes a first magnet and the opposite end of the strap portion 105 includes a second oppositely charged magnet); one or more buckle connectors (e.g., such that one end of the strap portion 105 includes one or more prong or tongue connectors that can engage one or more holes or openings on the opposite end of the strap portion 105); one or more ratchet connectors (e.g., such that one end of the strap portion includes a pawl or spring-loaded lever and the opposite end includes a toothed bar that is adapted to engage the pawl or spring-loaded lever); and/or one or more male/female connectors (e.g., such that one end of the strap portion 105 includes a male portion that can be connected to a female portion located of the opposite end of strap portion 105). Many other types of connection schemes also can be incorporated into the wearable armrest apparatus 100.

In some embodiments, the wearable armrest apparatus 100 may only include a single connector 110 to facilitate connection of the proximal end 103 to the distal end 104 of the strap portion 110. For example, in some scenarios, one end of the strap portion 150 may include a clamping mechanism that includes an opening for receiving an opposite end of the strap portion, and the clamping mechanism can be adjusted between an open and locked position. Other types of single connector arrangements also be utilized.

As shown in FIGS. 1A-1G and 2A-2I, a pair of armrest structures 150 extend outwardly from the exterior surface 101 of the strap portion 105 in a direction that is substantially perpendicular to the strap portion 105. Each of the armrest structures 150 can include a top resting surface 151 that is substantially flat or planar. When the wearable armrest apparatus 100 is worn around an individual's waist or torso in an assembled configuration 120, the armrest structures 150 are positioned directly beneath the individual's elbows and/or forearm regions and directly adjacent to the individual's waist or torso region. This enables the individual to rest easily and comfortably his or her elbows and/or forearms on the top surface 151.

The shape or configuration of the top surface 151 can vary. In some preferred embodiments, the top surface 151 is arranged in semi-circular or crescent-like shape that includes an outer perimeter having a convex curvature (such as a semicircular or arc-like curvature) and the inner perimeter having a concave curvature (see FIGS. 1C, 1D, 1F, 2C, 2D, 2E, and 2G). This shape or configuration of the top surface 151 can provide several benefits. When the strap portion 105 is worn by an individual, the concave inner surface can be situated near the individual's side regions (e.g., hips or lower abdomen sides) and the curvature of the surface accommodates individuals of different body types and improves comfortability. Additionally, the convex surfaces on the outer perimeter of the top surface 151 reduce the bulkiness of the armrest structures 150 and provide additional space for an individual's arms to hang freely (see FIG. 3D) when the armrest structures 150 are not being utilized.

The shape of the top surface 151 can vary in other embodiments. In some examples, the top surface 151 can be configured in a square, rectangular, and/or triangular shapes. In further examples, the top surface 151 can be configured in circular and/or oval-like shapes. The top surface 151 can be arranged in other configurations as well.

In certain embodiments, the top surfaces 151 of the armrest structures 150 are connected to the strap 105 at or near a top edge 109 of the strap portion 105. An outer surface 152 of the armrest structures 150 extends downwardly toward a bottom edge of the strap portion 105. In certain embodiments, the outer surface 152 includes a slope or curvature that gradually narrows or tapers inwardly toward the exterior surface 101 of the strap portion 105. The outer surface 152 can terminate or end at or near the bottom edge 109 of the strap portion 105.

Figure 2A:
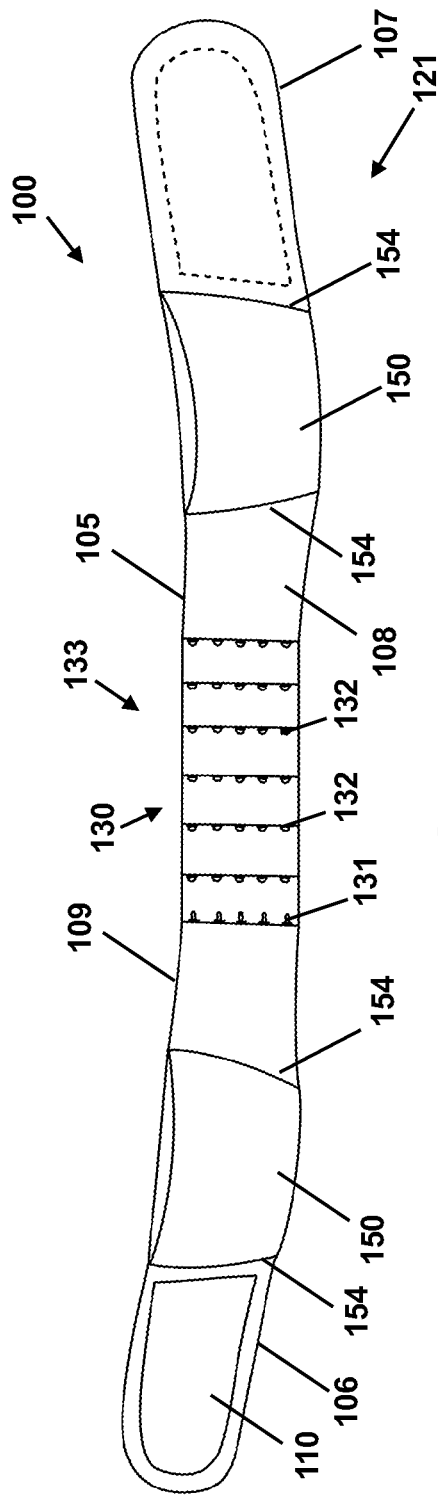
FIG. 2A is a front view of another wearable armrest apparatus that includes a size-adjustment feature arranged in an extended or disengaged configuration in accordance with certain embodiments.
Figure 2B:
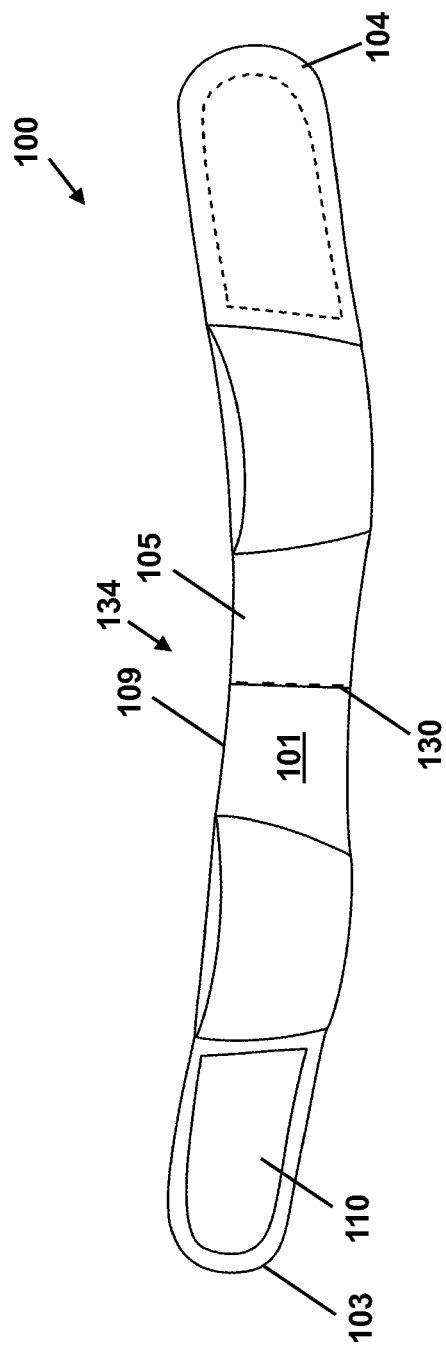
FIG. 2B is a front view of the wearable armrest apparatus in FIG. 2A in which the size-adjustment feature is arranged in a retracted or engaged configuration in accordance with certain embodiments.
Figure 2C:
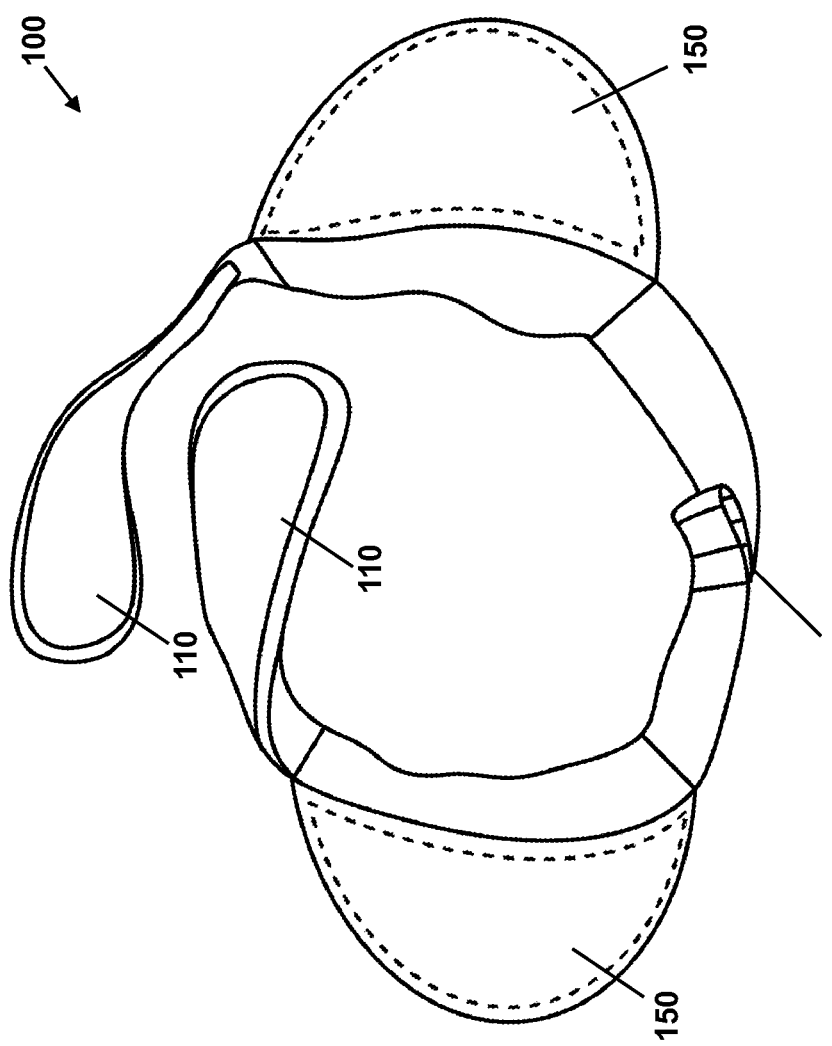
FIG. 2C is a top view of the wearable armrest apparatus illustrated in FIG. 2A with the size-adjustment feature arranged in the retracted or engaged configuration the in accordance with certain embodiments.
Figure 2G:
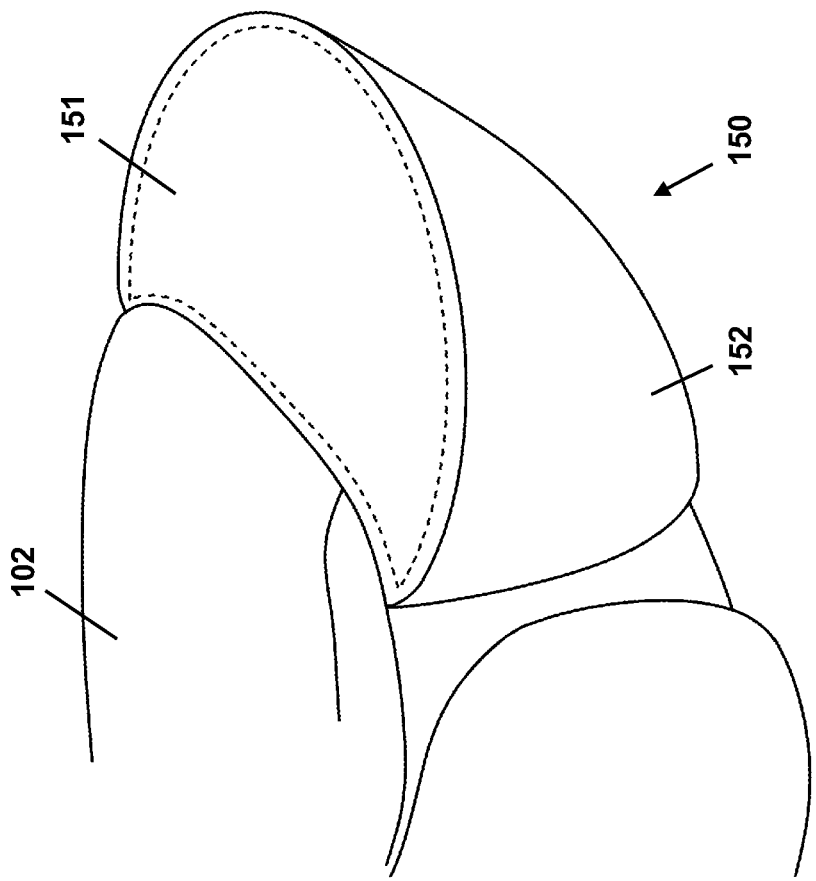
FIG. 2G is perspective view illustrating details of an exemplary armrest structure of the wearable armrest apparatus illustrated in FIG. 2A in accordance with certain embodiments.
Figure 2F:
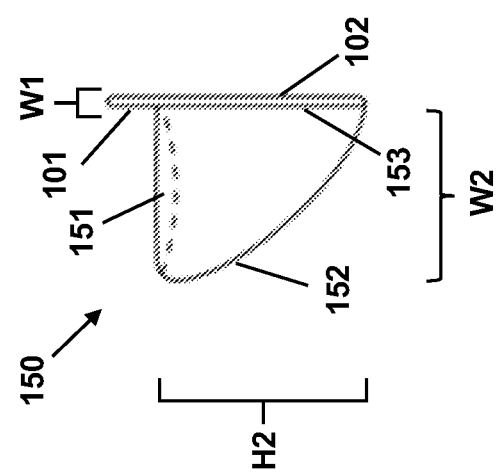
FIG. 2F is side view of the wearable armrest apparatus illustrated in FIG. 2A in accordance with certain embodiments.

Connecting edges 154 are formed at the locations where the armrest structures 150 connect the exterior surface 101. For example, as shown in FIGS. 1A and 2A, a first armrest structure 150 located nearest to the proximal end 103 includes a first connecting edge 154 at the boundary between the proximal exterior segment 106 and the leftmost portion of the first armrest structure 150, and also includes a second connecting edge 154 at the boundary between a leftmost portion of the middle exterior segment 108 and the rightmost portion of the first armrest structure 150. Similarly, a second armrest structure 150 located nearest to the distal end 104 includes a third connecting edge 154 at the boundary between the distal exterior segment 106 and the rightmost portion of the second armrest structure 150, and also includes a fourth connecting edge 154 at the boundary between a rightmost portion of the middle exterior segment 108 and the leftmost portion of the second armrest structure 150.

In some embodiments, inner connecting surfaces 153 (see FIGS. 1E and 2F) of the armrest structures 150 can be located on the inner portions of the armrest structures 150 at locations where the armrest structures 150 are connected to the strap portion 105. Like the inner perimeter of the top surface 151, the inner connecting surfaces 153 can be arranged in a concave shape, which can be beneficial to accommodate individuals having different body sizes and to promote comfortability when the wearable armrest apparatus is worn.

The area or interior of each armrest structure 150 (inside the area formed by the top surface 151, outer surface 152, and inner connecting surface 153) can include a semi-rigid or rigid material that can serve to support an individual's elbows and/or forearms. In some embodiments, the interior of the armrest structures 150 can be filled with foam material (e.g., memory foam, polyurethane foam, latex foam, gel-infused foam, and/or other types of foam materials). Additionally, or alternatively, the interior of the armrest structures 150 can be filled other materials (e.g., such as polymers, plastics, woods, metals, etc.). In some embodiments, the interior of the armrest structures 150 can be filled with a light-weight foam (e.g., polyethylene foam, expanded polystyrene foam, polyurethane foam, etc.) to reduce the weight of the wearable armrest apparatus 100.

The surfaces of the armrest structure 150, including the top surface 151, outer surface 152, and connecting surface 153, can be constructed of various materials. In some embodiments, these surfaces can be constructed from the same or similar materials utilized to construct the strap portion 105 (e.g., such as cotton fibers, synthetic fibers, wool fibers, linen fibers, microfibers, etc.).

The dimensions of the armrest structures 150 can vary. In some embodiments, the width W2 of each armrest structure 150 (or top surface 151) can extend approximately 4 inches away from the strap portion 105 and/or within a range of approximately 3-7 inches away from the strap portion 105 (see FIGS. 1E and 2F). The height H2 of each armrest structure 150 (and/or inner connecting surface 153) can be approximately 5.5 inches and/or within a range of 2-8 inches (see FIGS. 1E and 2F), and the length L2 of each armrest structure 150 can be approximately 7.5 inches and/or within a range of 4-10 inches (see FIGS. 1D, 2D and 2E). Other dimensions also may be utilized for the design of the armrest structures 150.

Figure 1G:
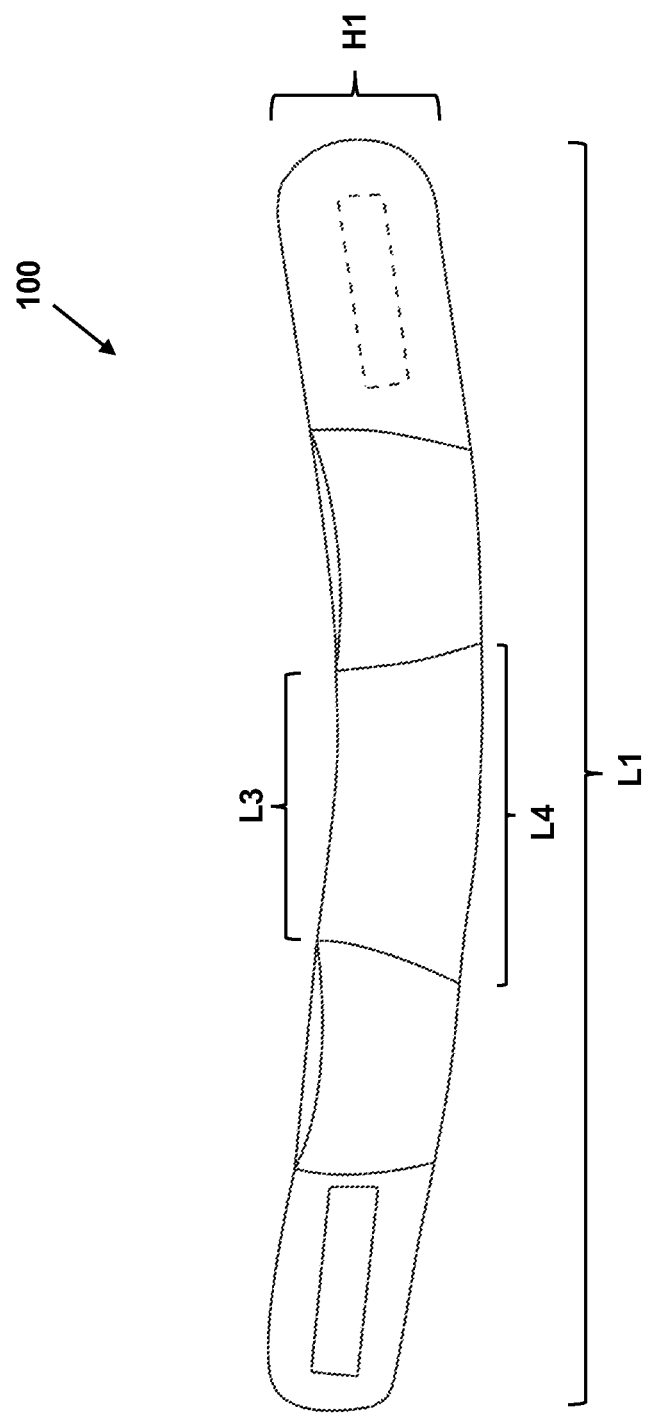
FIG. 1G is another front view of the wearable armrest apparatus illustrated in FIG. 1A in accordance with certain embodiments.

As shown in FIGS. 1G, 2H, and 2I, the portion of the top edge 109 extending between the first armrest structure 150 and the second armrest structure 150 has a first length L3, and the portion of the bottom edge 109 extending between the first armrest structure 150 and the second armrest structure 150 has a second length L4, which can be different from the first length L3. As shown, the first length L3 is smaller than the second length L4.

In certain embodiments, the armrest structures 150 can be located at strategic positions along the exterior surface 101, such as to position the armrest structures 150 directly beneath an individual's elbows and/or forearms when the wearable armrest apparatus is worn by the individual. In certain embodiments, the first armrest structure 150 (or either of the first or second connecting edges 154 of the first armrest structure 150) located nearest to the proximal end 103 can be located approximately 15-35% along the length of the strap portion 105 away from the proximal end 103 and/or 65-85% along the length of the strap portion 105 away from the distal end 104. In one example, the strap portion 105 may have a length L1 of approximately 48 inches, and the first connecting edge 154 and/or the armrest structure 150 may be distanced approximately 8.5 inches (or in a range of 5.5-11.5 inches) away from the proximal end 103 and approximately 39.5 inches (or in a range of 36.5-42.5 inches) away from the distal end 104. Similarly, the second armrest structure 150 (or either of the third or fourth connecting edges 154 of the second armrest structure 150) located nearest the distal end 104 can be located 15-35% along the length of the strap portion 105 away from the distal end 104 (e.g., distanced approximately 8.5 inches, or in a range of 5.5-11.5 inches, away from the distal end 104 if the strap portion is 48 inches) and/or 65-85% along the length of the strap portion 105 away from the proximal end 103 (e.g., distanced approximately 39.5 inches, or in a range of 36.5-42.5 inches, away from the proximal end 103 if the strap portion is 48 inches). Strategically positioning the armrest structures 150 at these locations along the strap portion 105 can enable the armrest structures 150 to be situated at optimal locations for supporting an individual's arms (e.g., elbows and/or forearms) when the wearable armrest apparatus 150 is worn in an assembled configuration 120 and the individual is performing various activities that require the individual's arms to be extended. Additionally, as explained below, the strap portion 105 can include a size-adjustment assembly 130 that enables the wearable armrest apparatus 100 to be fitted to individuals of various sizes, and permits the locations of the armrest structures 150 to be more precisely aligned beneath individuals' elbows.

The armrest structures 150 can be connected to, or integrated with, the strap portion 105 in various ways. In some embodiments, each of the armrest structures 150 can be sewn or stitched onto to the strap portion 105 and/or exterior surface 101 using various techniques (e.g., top stitching, edge stitching, invisible stitching, fusible interfacing, and/or other techniques). Additionally, or alternatively, the armrest structures 150 can be connected to the strap portion 105 using adhesives (e.g., fabric glues, fabric cements, heat-activated adhesives, fabric tapes, double-sided tapes, etc.). The armrest structures 150 can be connected to the strap portions 105 using other techniques as well.

In certain embodiments, such as where the strap portion 105 or exterior surface 101 is composed of multiple segments, the side edges of the armrest structures 150 can be connected (e.g., stitched, sewn, adhered, etc.) to the side edges of strap portion segments (e.g., proximal, middle, and distal segments).

In certain embodiments, the strap portion 105 can include a size-adjustment assembly 130 (see example in FIGS. 2A-2I) that enables the strap portion 105 to be tightened or loosened around an individual's waist or torso region and/or that enables wearable armrest apparatus 100 to be fitted to individuals of various sizes. Additionally, the size-adjustment assembly 130 permits the locations of the armrest structures 150 to be more precisely aligned beneath individuals' elbows.

In some embodiments, the size-adjustment assembly 130 can be located on the middle exterior segment 108 of the strap portion 105. In other embodiments, the size-adjustment assembly 130 can be included on other portions of wearable armrest apparatus 100 (e.g., such as on or near the proximal end 103 or the distal end 104 of the strap portion 105).

The configuration of the size-adjustment assembly 130 can vary. In some embodiments, the size-adjustment assembly 130 comprises one or more hook connectors 131 that are configured to engage one or more loop connectors 132. In the example illustrated in the drawings, the size-adjustment assembly 130 comprises a column of multiple hook connectors 131 (e.g., five hook connectors) that are arranged vertically on the strap portion 105, and multiple columns of loop connectors 132 (e.g., each of which includes five loop connectors that are configured to be coupled to the hook connectors 131). The columns of loop connectors 132 are separated by a distance (e.g., half inch, inch, or other distance), and each column corresponds to length setting. An individual can choose the desired length setting for the strap portion 105 by coupling the hook connectors 131 to the loop connectors 132 included in a column corresponding to the desired length setting.

The size-adjustment assembly 130 can be configured in a disengaged configuration 133 (see FIGS. 2A and 2H) in which the hook connectors 131 are not coupled to any loop connectors 132), and can be transitioned to an engaged configuration 134 in which at least one hook connector 131 is coupled to at least one loop connector 132 (or in which a column of hook connectors 131 is coupled to one column of loop connectors 132). Because the circumference of waists and torsos regions can vary across individuals, an individual can couple the column of hook connectors 131 to a column of loop connectors 132 that provides the best fit for the individual. In addition to fitting the strap portion 105 to the size of the individual's waist or torso, the coupling of the hook connectors 131 to the loop connectors 132 can serve to adjust the position of the armrest structures 150 to be situated directly beneath the individual's elbows.

In some examples, the first length L3 of the top edge 109 extending between the first armrest structure 150 and the second armrest structure 150 may be approximately 16 inches (or in a range of 13-19 inches) and the second length L4 may be approximately 20 inches (or in a range of 17-23 inches) when the strap portion 105 is fully extended and the size-adjustment feature is arranged in a disengaged configuration 133. When the size-adjustment feature is arranged in an engaged configuration 134, the first length L3 may be approximately 10 inches (or in a range of 7-13 inches) and the second length L4 may be approximately 14 inches (or in a range of 11-17 inches).

It should be recognized that the size-adjustment feature 130 can be modified in various ways to facilitate adjustment of the strap portion 105. In some examples, other types of connectors (e.g., snap connectors, button connectors, belt connectors, etc.) can be incorporated into the strap portion 105 instead of, or in addition to, the hook connectors 131 and loop connectors 132 illustrated in FIGS. 2A-2I. Additionally, in some examples, the size-adjustment assembly 130 can include one or more drawstrings that can be used to cinch or tighten the strap portion 105 around an individual's waist or torso region. In further examples, the size-adjustment assembly 130 can include a ruching-based design configuration that includes an adjustable strap, and this configuration can be incorporated into one or more segments or sections of the strap portion 105. In further examples, the size-adjustment assembly 130 can incorporate a shirring-based design configuration into one or more segments or sections of the strap portion 105, which can be configured with elasticity to accommodate different size waists or torsos. In further examples, the size-adjustment assembly 130 can incorporate a smocking-based design configuration into one or more segments or sections of the strap portion 105, which can be provide a degree of stretchability or flexibility to accommodate different size waists or torsos.

Additionally, the size-adjustment feature 130 can integrated into other regions of strap portion 105 (e.g., on the interior surface 102 or near the proximal and/or distal ends of the strap portion). Depending on the configuration of the size-adjustment feature 130, the size-adjustment feature 130 also can extend the length (or a majority of the length) of the strap portion 105 (e.g., such as when shirring segment is incorporated). Other modifications or variations are also possible.

The armrest structures 150 are designed with several ergonomic enhancements that reduce strain on an individual's body and improve comfortability. One major benefit is the ability of an individual to support his or arms comfortably on the top resting surfaces 151 of the armrest structures 150 while performing various activities that require extension of the individual's arms (e.g., while operating a computing device, preparing food, holding a fishing rod, etc.). Additionally, the angle of the top resting surfaces 151 (e.g., approximately 90 degrees with respect to the strap portion 105) and positioning of the armrest structures 150 along the exterior surface at optimal locations serves to maintain a neutral positioning of the individual's arms. In many embodiments, the locations of the armrest structures 150 can be situated at a position that creates an obtuse angle between the individual's biceps and the forearms when the individual's arms are rested on the armrest structures. In certain embodiments, the precise location of the armrest structures along the strap portion 150 can be positioned between a geometric midpoint of the individual (e.g., the lumber region of the individual's spine or back and/or the individual's waist region) and the farthest extension of the individual's arms from the shoulders in order to minimize strain and maximize comfortability on the individual.

Positioning or situating the armrest structures 150 along the strap portion 105 according to the techniques described herein can reduce the strain on the individual's the muscle groups in the neck, shoulder, and upper back regions. Additionally, it can reduce the strain in these muscle groups more effectively than traditional armrests that are integrated into seating assemblies or other stationary structures due to the fact that the individual does not need to laterally or vertically displace his or her elbows or forearms. In contrast, the armrest structures 150 of the wearable armrest apparatus 100 can be provided in a body-hugging configuration that enables an individual's elbows and forearms to be supported directly adjacent to the individual's body (e.g., directly adjacent to the individual's waist or lower torso region), which serves to maintain the individual's shoulder joints and associated musculoskeletal system in a neutral position (or very close to a neutral position).

Additionally, the design of the wearable armrest apparatus 100 can be optimized to provide form-fitting capabilities that accommodate individuals having various body types. These form-fitting advantages can be attributed, at least in part, to the concave curvature of the inner connecting surfaces 153 and inner perimeter of the top surface 151 on the armrest structures 150, which enable the wearable armrest apparatus 100 to comfortably accommodate different body types. In certain embodiments, the adjustability of the strap portion 105 using the size-adjustment assembly 130 also contributes to the form-fitting capabilities. Regardless of the individual's body type or size, the armrest structures 150 can be moved or positioned to optimal locations to enable a neutral positioning of the individual's arms.

Other design aspects that contribute to the form-fitting capabilities of the wearable armrest apparatus 100 include the configuration of the connectors 110, which can be adjustable to customize the size of the loop arrangement formed when connecting the proximal end 103 to the distal end 104 of the wearable armrest apparatus 100. Additionally, in some embodiments, the strap portion (or certain segments thereof) can be constructed of flexible or stretchable materials that further enhance the form-fitting capabilities of the wearable armrest apparatus 100.

Prototyping and testing have demonstrated that the size or dimensions of the armrest structures 150 can be optimized to provide several benefits. As explained above, the width W2 can be adapted to extend approximately 4 inches (or within a range of 3-7 inches), which can provide the benefit that an individual's arms may hang comfortably next to the armrest structures 150 (while the armrest structures 150 are not used for support) without being significantly impeded (see FIG. 3D). Additionally, the sloped or tapered curvature of the outer surface 152 can avoid bulkiness of the armrest structures 154, reduce the amount of material (e.g., foam material) needed to fill the interior of the armrest structure 150, and reduce the weight of the wearable armrest apparatus 100.

In FIGS. 1A-1G and 2A-2I illustrate the wearable armrest apparatus 100 in a disassembled configuration 121. In the disassembled configuration 121, the proximal end 103 of the strap portion 105 is disconnected from the distal end 104 of the strap portion 105 and/or the connector(s) included on the wearable armrest apparatus 100 are disengaged or released.

FIGS. 3A-3E illustrate the wearable armrest apparatus 100 in an assembled configuration 120. In the assembled configuration 120, the proximal end 103 of the strap portion 105 is connected to the distal end 104 of the strap portion 105 and/or the connector(s) included on the wearable armrest apparatus 100 are engaged to arrange the strap portion 105 in a loop arrangement.

In the examples illustrated in the drawings, a first end of the strap portion 105 may be folded over or situated on top of a second end of the strap portion 105. In this arrangement, a connector 110 located on the interior surface 102 of the first end engages, and couples to, a corresponding connector 110 located on the exterior surface 101 of the second end, which is tucked behind the first end of the strap portion 105. As mentioned above, various types of connectors 110 can be utilized (e.g., hook-and-loop connectors, button connectors, snap fit connectors, etc.) to couple the first end of the strap portion 105 to the second end of the strap portion 105.

FIGS. 3B-3D illustrate the wearable armrest apparatus 100 worn around an individual's waist or lower torso region in an assembled configuration 120. When the wearable armrest apparatus 100 is worn, the armrest structures are located directly beneath the individual's elbows and/or upper forearm regions and directly adjacent to the individual's waist or lower torso region.

FIG. 3B illustrates how the wearable armrest apparatus 100 can support the individual's elbows and/or forearms when the individual's arms are in an extended position. As shown, armrest structures 150 are positioned to maintain a neutral positioning of the individual's arms, thereby eliminating or reducing stress on the individual's muscles and joints in the in the neck, shoulder, and upper back regions. The positioning of the armrest structures 150 creates an obtuse angle A between the individual's biceps and the forearms when the individual's arms are rested on the armrest structures.

The armrest structures 150 of the wearable armrest apparatus 100 can be constructed of semi-rigid materials, such as foams or the like, that enable the armrest structures 150 to deform to some extent in response to the weight of the individual's arms. In some examples, memory foams or the like can enable deformation of the armrest structures 150 when the armrest structures 150 are supporting the individual's arms, and then the armrest structures 150 can return to their original shape when armrest structures 150 are not being utilized to support the individual's arms.

When using the armrest structures 150 to support the individual's arms, the top surfaces 151 of the armrests can deform slightly to receive and accommodate the shape of the individual's arms. Likewise, the front edge regions B (where the individual's forearms are extended forward) of the armrest structures 150 can deform to accommodate the individual's forearms and provide for comfort.

FIG. 3C illustrates the wearable armrest apparatus 100 worn around an individual's waist or torso region when the individual's arms are placed in a rearward position (e.g., behind the individual's back). The dimensions and positioning of the armrest structures 150 permit the individual's arms to easily be transitioned to this rearward position and do not impede movement of the individual's arms.

FIG. 3D illustrates the wearable armrest apparatus 100 worn around an individual's waist or torso region when the individual's arms in a side or hanging position. Again, the dimensions and positioning of the armrest structures 150 permit the individual's arms to comfortably hang without being impeded by the armrest structures 150. The length L2 of each armrest structure 150 can be selected appropriately to permit the individual's arms to comfortably hang by his or her side without being impeded by the armrest structures 150. Testing and prototyping have shown that the length L2 of each armrest structure 150 extending outward from the strap portion 105 can be approximately 7.5 inches and/or within a range of 4-10 inches to provide this benefit.

Figure 4:
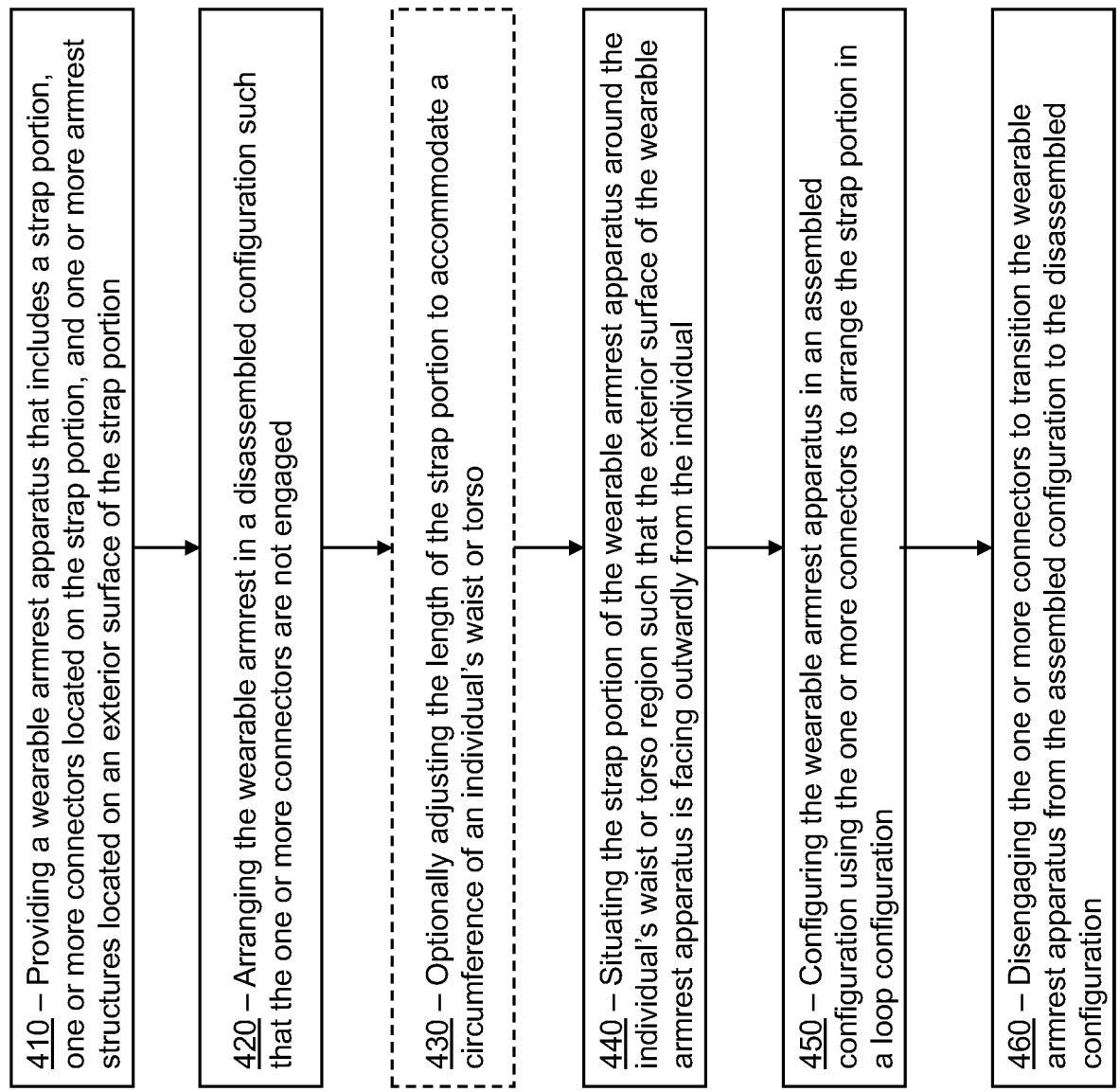
FIG. 4 is a flowchart illustrating an exemplary method for equipping and using a wearable armrest apparatus in accordance with certain embodiments.

FIG. 4 illustrates a flow chart for an exemplary method 400 for equipping and using a wearable armrest apparatus 100 according to certain embodiments. Method 400 is merely exemplary and is not limited to the embodiments presented herein. Method 400 can be employed in many different embodiments or examples not specifically depicted or described herein. In some embodiments, the steps of method 400 can be performed in the order presented. In other embodiments, the activities of method 400 can be performed in any suitable order. In still other embodiments, one or more of the steps of method 400 can be combined or skipped. In many embodiments, an individual utilizing the armrest apparatus 110 can be configured to perform method 400 and/or one or more of the steps of method 400.

In step 410, a wearable armrest apparatus 100 is provided that includes a strap portion 105, one or more connectors 110 located on the strap portion 105, and one or more armrest structures 150 connected to an exterior surface 191 of the strap portion 105.

In step 420, the wearable armrest 100 is arranged in a disassembled configuration 121 such that the one or more connectors 110 are not engaged.

In optional step 430, the length of the strap portion is adjusted to accommodate a size or circumference of an individual's waist or torso. The length may be adjusted using the size-adjustment assembly 130 described above.

In step 440, the strap portion 105 of the wearable armrest apparatus 100 is situated around the individual's waist or torso region such that the exterior surface 101 of the wearable armrest apparatus 100 is facing outwardly from the individual.

In step 450, the wearable armrest apparatus is reconfigured in an assembled configuration 120 using the one or more connectors to arrange the strap portion in a loop configuration. In the assembled configuration 120, the armrest structures 150 located on the exterior surface 101 of the strap portion 105 are situated directly beneath an individual's elbows and/or forearms. The individual can rest his or her elbows and/or forearms on the armrest structures 150 while performing various tasks or activities.

In step 460, the one or more connectors are disengaged to transition the wearable armrest apparatus 100 from the assembled configuration 120 to the disassembled configuration 121.

In certain embodiments, a wearable armrest apparatus comprises: (a) a strap portion comprising an interior surface and an exterior surface, wherein both the interior surface and the exterior surface extend between a proximal end and a distal end of the strap portion; (b) a pair of armrest structures coupled to the exterior surface of the strap portion, each of the armrest structures comprising a top resting surface that is adapted to receive the individual's elbows or forearms in an assembled configuration; and (c) at least one connector included on the strap portion, the at least one connector being configured to secure the strap portion around an individual's waist or torso region when arranged in the assembled configuration.

In certain embodiments, a wearable armrest apparatus comprises: (a) a strap portion comprising an interior surface and an exterior surface, wherein the interior surface and the exterior surface have a length extending between a first end and a second end of the strap portion, and the strap portion is configured to be worn around an individual's waist or torso in an assembled configuration; (b) a first armrest structure extending outwardly from the exterior surface of the strap portion, wherein: (i) the first armrest structure is located approximately 15-25% along the length of the strap portion with respect to the first end; and (ii) the first armrest structure includes a first top surface that is substantially perpendicular to the exterior surface; (c) a second armrest structure extending outwardly from the exterior surface of the strap portion, wherein: (i) the second armrest structure is located approximately 15-25% along the length of the strap portion with respect to the second end; and (ii) the second armrest structure includes a second top surface that is substantially perpendicular to the exterior surface; and (d) one or more connectors attached to the strap portion, the one or more connectors enabling the strap portion to be connected around the individual's waist or torso in the assembled configuration.

In certain embodiments, a mobile armrest apparatus comprises: (a) a strap portion configured to be worn around an individual's waist or torso region in an assembled configuration, the strap portion comprising: (i) an interior surface extending between a proximal end and a distal end of the strap portion; and (ii) an exterior surface extending between the proximal end and the distal end of the strap portion; (b) at least one armrest structure extending outwardly from the exterior surface of the strap portion, wherein: (i) the at least one armrest structure includes a top resting surface; (ii) the top resting surface of the at least one armrest structure is substantially flat or planar; and (ii) the top resting surface of the at least one armrest structure is situated an angle that is substantially perpendicular to the strap portion.

In certain embodiments, a mobile armrest apparatus comprises: (a) a strap portion configured to be worn around an individual's waist or torso region in an assembled configuration, the strap portion comprising: (i) an interior surface extending between a proximal end and a distal end of the strap portion; and (ii) an exterior surface extending between the proximal end and the distal end of the strap portion; and (b) at least one armrest structure extending outwardly from the exterior surface of the strap portion, wherein the at least one armrest structure includes a top resting surface that is adapted to support an individual's elbow or forearm when the strap portion is arranged in the assembled configuration and worn around the individual's waist or torso region.

In certain embodiments, a wearable or mobile armrest apparatus comprises: (a) a strap portion; (b) a first armrest structure coupled to an exterior surface of the strap portion; (c) a second armrest structure coupled to the exterior surface of the strap portion; and (d) at least one connector that enables a proximal end of the strap portion to be releasably coupled to a distal end of the strap portion.

In certain embodiments, a wearable or mobile armrest apparatus comprises: (a) a strap portion; (b) at least one armrest structure extending from an exterior surface of the strap portion; and (c) at least one connector that enables a proximal end of the strap portion to be connected to a distal end of the strap portion.

While various novel features of the invention have been shown, described, and pointed out as applied to particular embodiments thereof, it should be understood that various omissions and substitutions, and changes in the form and details of the systems and methods described and illustrated, may be made by those skilled in the art without departing from the spirit of the invention. Amongst other things, the steps in the methods may be carried out in different orders in many cases where such may be appropriate. Those skilled in the art will recognize, based on the above disclosure and an understanding of the teachings of the invention, that the particular hardware and devices that are part of the system described herein, and the general functionality provided by and incorporated therein, may vary in different embodiments of the invention. Accordingly, the description of system components is for illustrative purposes to facilitate a full and complete understanding and appreciation of the various aspects and functionality of particular embodiments of the invention as realized in system and method embodiments thereof. Those skilled in the art will appreciate that the invention can be practiced in other than the described embodiments, which are presented for purposes of illustration and not limitation. Variations, modifications, and other implementations of what is described herein may occur to those of ordinary skill in the art without departing from the spirit and scope of the present invention and its claims.

The invention claimed is:

1. A wearable armrest apparatus comprising:
   a strap portion comprising an interior surface and an exterior surface, wherein both the interior surface and the exterior surface extend between a proximal end and a distal end of the strap portion;
   a pair of armrest structures fixedly connected to the exterior surface of the strap portion in a non-adjustable fashion, wherein:
      each of the armrest structures comprise a top resting surface that is adapted to receive an individual's elbows or forearms in an assembled configuration; and
      each of the armrest structures further comprise an outer surface that extends downwardly and inwardly from the top resting surface and which connects to the strap portion at or near a bottom edge of the strap portion;
   at least one connector included on the strap portion, the at least one connector being configured to secure the strap portion around an individual's waist or torso region when arranged in the assembled configuration; and
   an adjustment assembly located on the exterior surface of the strap portion between the pair of armrest structures, wherein the adjustment assembly enables the pair of armrest structures attached to the strap portion to be repositioned and aligned beneath the individual's elbows or forearms.

2. The wearable armrest apparatus of claim 1, wherein:
the top resting surface of each armrest structure is substantially flat or planar;
the top resting surface of each armrest structure is situated at an angle that is substantially perpendicular to the strap portion; and
the top resting surface of each armrest structure extends outwardly from the exterior surface of strap portion in range of 3 inches to 7 inches.

3. The wearable armrest apparatus of claim 1, wherein:
each of the armrest structures include a connecting surface that is in contact with the exterior surface of the strap portion; and
the connecting surface has a concave curvature adapted to accommodate a side region of the individual's waist or torso region when the wearable armrest apparatus is configured in the assembled configuration.

4. The wearable armrest apparatus of claim 1, wherein:
the pair of armrest structures include: (i) a first armrest structure comprising a first connecting edge and a second connecting edge; and (ii) a second armrest structure comprising a third connecting edge and a fourth connecting edge;
the exterior surface comprises a proximal exterior segment, a middle segment, and a distal exterior segment;
the proximal exterior segment extends from the proximal end of the strap portion to the first connecting edge of the first armrest structure;
the middle segment extends between the second connecting edge of the first armrest structure and the third connecting edge of the second armrest structure; and
the distal exterior segment extends between the distal end of the strap portion and the fourth connecting edge.

5. The wearable armrest apparatus of claim 4, wherein:
the first armrest structure is situated between the proximal exterior segment and the middle segment;
the second armrest structure is situated between the distal exterior segment and the middle segment;
the strap portion has a length extending from the proximal end to the distal end;
the first armrest structure is located approximately 15-35% along the length of the strap portion with respect to the proximal end; and
the second armrest structure is located approximately 65-85% along the length of the strap portion with respect to the proximal end.

6. The wearable armrest apparatus of claim 1, wherein:
the pair of armrest structures include a first armrest structure and a second armrest structure; and
the strap portion comprises a middle segment located between the first armrest structure and the second armrest structure.

7. The wearable armrest apparatus of claim 6, wherein:
the strap portion includes a top edge and bottom edge;
a portion of the top edge extending between the first armrest structure and the second armrest structure has a first length;
a portion of the bottom edge extending between the first armrest structure and the second armrest structure has a second length; and
the first length and the second length are different.

8. The wearable armrest apparatus of claim 1, wherein the at least one connector comprises a pair of connectors included on the strap portion, the pair of connectors comprising a first connector situated on or near the proximal end of the strap portion and a second connector situated on or near the distal end of the strap portion, wherein the first connector and the second connector are configured to be coupled to each other in the assembled configuration.

9. A wearable armrest apparatus comprising:
a strap portion comprising an interior surface and an exterior surface, wherein the interior surface and the exterior surface have a length extending between a first end and a second end of the strap portion, and the strap portion is configured to be worn around an individual's waist or torso in an assembled configuration;
a first armrest structure affixed to the exterior surface of the strap portion at a first location and extending outwardly from the exterior surface of the strap portion, wherein:
the first location of the first armrest structure is positioned approximately 15-35% along the length of the strap portion with respect to the first end; and
the first armrest structure includes a first top surface that is substantially perpendicular to the exterior surface;
a second armrest structure affixed to the exterior surface of the strap portion at a second location and extending outwardly from the exterior surface of the strap portion, wherein:
the second location of the second armrest structure is positioned approximately 65-85% along the length of the strap portion with respect to the first end; and
the second armrest structure includes a second top surface that is substantially perpendicular to the exterior surface; and
one or more connectors attached to the strap portion, the one or more connectors enabling the strap portion to be connected around the individual's waist or torso in the assembled configuration;
wherein, when configured in the assembled configuration, the first location of the first armrest structure and the second location of the second armrest structure enable the individual's elbows to be supported in a neutral position while the individual's hands are extended forward in front of the individual.

10. The wearable armrest apparatus of claim 9, wherein:
the first top surface and the second top surface are both substantially flat or planar; and
the first top surface and the second top surface both extend outwardly from the exterior surface of strap portion.

11. The wearable armrest apparatus of claim 10, wherein:
the strap portion includes a top edge and a bottom edge;
the first top surface and the second top surface are both located along the strap portion at or near the top edge of the strap portion;
the first armrest structure and the second armrest structure each include an outer surface that extends downwardly from the first top surface and second top surface, respectively;
the outer surface includes a curvature that extends inwardly towards the strap portion; and
the outer surface connects to the strap portion at or near the bottom edge of the strap portion.

12. The wearable armrest apparatus of claim 9, wherein the first armrest structure and the second armrest structure both include a curved surface that is adapted to accommodate a side region of the individual's waist or torso when the wearable armrest apparatus is configured in the assembled configuration.

13. The wearable armrest apparatus of claim 9, wherein:
the exterior surface comprises a proximal exterior segment, a middle segment, and a distal exterior segment;
the proximal exterior segment extends from the first end of the strap portion to the first armrest structure;
the middle segment extends between the first armrest structure and the second armrest structure; and
the distal exterior segment extends between the second end of the strap portion and the second armrest structure.

14. The wearable armrest apparatus of claim 9, wherein the strap portion comprises an adjustment assembly that enables the strap portion to be arranged in different sizes or lengths and which enables repositioning of the first armrest structure and the second armrest structure.

15. The wearable armrest apparatus of claim 9, wherein the first armrest structure and the second armrest structure are adapted to:
support the individual's elbows when the individual's hands are extended forward in front of the individual, allowing the individual's hands to be freely used in a forward position; and
permit the individual's arms to hang freely by the individual's sides when the armrest structures are not being used to support the individual's elbows;
wherein the first armrest structure and the second armrest structure each have a length that is sufficient to support the individual's elbows while being short enough to avoid impeding the individual's arms when hanging freely by the individual's sides; and
wherein a configuration of wearable armrest apparatus permits the first and second armrest structures to be positioned along the strap portion such that, when the individual's arms are rested on the first and second armrest structures, an obtuse angle is created between the individual's biceps and forearms to provide the neutral position of the individual's arms.

16. The wearable armrest apparatus of claim 9, wherein the first armrest structure and the second armrest structure each extend along the exterior surface a length of approximately 7.5 inches, and each have an outer surface that extends downwardly and inwardly from the first top surface and the second top surface, respectively, toward the strap portion.

17. A mobile armrest apparatus comprising:
a strap portion configured to be worn around an individual's waist or torso region in an assembled configuration, the strap portion comprising:
an interior surface extending between a proximal end and a distal end of the strap portion; and
an exterior surface extending between the proximal end and the distal end of the strap portion; and
at least one armrest structure directly coupled to the exterior surface of the strap portion and extending outwardly from the exterior surface of the strap portion, wherein:
the at least one armrest structure includes a top resting surface;
the top resting surface of the at least one armrest structure is substantially flat or planar;
the top resting surface of the at least one armrest structure is situated at an angle that is substantially perpendicular to the strap portion;
the top resting surface is arranged in semi-circular or crescent-type shape that includes an outer perimeter having a convex curvature;
a length of the at least one armrest structure is approximately 7.5 inches; and
an outer surface of the at least one armrest structure extends downwardly and inwardly from the top resting surface and connects to the strap portion.

18. The mobile armrest apparatus of claim 17, wherein the at least one armrest structure includes:
a first armrest structure fixed to the exterior surface and extending outwardly from a first location on the exterior surface of the strap portion; and
a second armrest structure that extends outwardly from a second location on the exterior surface of the strap portion;
wherein the first location and the second location correspond to positions that maintain a neutral positioning of the individual's arms when the individual's elbows are supported by the first armrest structure and the second armrest structure.

19. The mobile armrest apparatus of claim 17, wherein the at least one armrest structure includes a curved surface that is adapted to accommodate a side region of the individual's waist or torso region when the mobile armrest apparatus is configured in the assembled configuration.

20. The mobile armrest apparatus of claim 17, wherein the exterior surface comprises an adjustment assembly that enables the strap portion to be arranged in different sizes or lengths and which enables the at least one armrest structure to be repositioned.

* * * * *